US011957794B2

(12) United States Patent
Sukhorukov et al.

(10) Patent No.: US 11,957,794 B2
(45) Date of Patent: *Apr. 16, 2024

(54) BIODEGRADABLE MULTILAYER NANOCAPSULES FOR THE DELIVERY OF BIOLOGICALLY ACTIVE AGENTS IN TARGET CELLS

(71) Applicants: Albert-Ludwigs-Universitaet Freiburg, Freiburg (DE); Queen Mary University of London, London (GB)

(72) Inventors: Gleb Sukhorukov, Loughton (GB); Irina Nazarenko, Glottertal (DE); Yana Tarakanchikova, Engels (RU); Toni Cathomen, Freiburg (DE); Tatjana Cornu, Freiburg (DE); Valentina Pennucci, Freiburg (DE); Jamal Alzubi, Freiburg (DE)

(73) Assignees: Albert-Ludwigs-Universitaet Freiburg, Freiburg (DE); Queen Mary University of London, London (GB)

( * ) Notice: Subject to any disclaimer, the term of this patent is extended or adjusted under 35 U.S.C. 154(b) by 179 days.

This patent is subject to a terminal disclaimer.

(21) Appl. No.: 17/574,933

(22) Filed: Jan. 13, 2022

(65) Prior Publication Data
US 2022/0233462 A1   Jul. 28, 2022

Related U.S. Application Data

(63) Continuation of application No. 16/634,060, filed as application No. PCT/EP2018/070111 on Jul. 25, 2018, now Pat. No. 11,253,482.

(30) Foreign Application Priority Data

Jul. 26, 2017 (EP) .................................. 17183188

(51) Int. Cl.
 *A61K 9/51* (2006.01)
 *A61K 31/7105* (2006.01)
 (Continued)

(52) U.S. Cl.
 CPC .......... *A61K 9/5161* (2013.01); *A61K 9/5146* (2013.01); *A61K 9/5192* (2013.01);
 (Continued)

(58) Field of Classification Search
 None
 See application file for complete search history.

(56) References Cited

U.S. PATENT DOCUMENTS

| 11,253,482 B2 * | 2/2022 | Sukhorukov ...... A61K 47/6455 |
| 2003/0219384 A1 * | 11/2003 | Donath ................ A61K 9/5026 424/94.1 |

(Continued)

FOREIGN PATENT DOCUMENTS

| WO | WO 2015/088445 | 6/2015 |
| WO | WO 2015/089419 | 6/2015 |

(Continued)

OTHER PUBLICATIONS

Akihiro Kishimura. "Development of polyion complex vesicles (PICsomes) from block copolymers for biomedical applications." Polymer Journal, vol. 45, 2013, pp. 892-897. (Year: 2013).*

(Continued)

*Primary Examiner* — Isaac Shomer
(74) *Attorney, Agent, or Firm* — Smith Patent, LLC; Chalin A. Smith

(57) ABSTRACT

The present invention relates to a biodegradable multilayer nanocapsule for the delivery of at least one biologically active agent into at least one target cell consisting of at least two layers of at least two biodegradable polymers which are laid one onto the other and whereby the biologically active (Continued)

agent is layered onto a layer of a biodegradable polymer and covered with a further layer of a biodegradable polymer, whereby one biologically active agent is a nucleic acid.

17 Claims, 26 Drawing Sheets

Specification includes a Sequence Listing.

(51) Int. Cl.
 *A61K 31/711* (2006.01)
 *B82Y 5/00* (2011.01)
(52) U.S. Cl.
 CPC ........ *A61K 31/7105* (2013.01); *A61K 31/711* (2013.01); *B82Y 5/00* (2013.01); *Y10S 977/773* (2013.01); *Y10S 977/906* (2013.01)

(56) References Cited

U.S. PATENT DOCUMENTS

| | | |
|---|---|---|
| 2011/0229576 A1 | 9/2011 | Trogler et al. |
| 2016/0120158 A1* | 5/2016 | Rabb ................. A01K 67/0276 800/9 |
| 2017/0128558 A1 | 5/2017 | Boyd |

FOREIGN PATENT DOCUMENTS

| | | | | |
|---|---|---|---|---|
| WO | WO-2015088445 A1 * | 6/2015 | ........... | A61K 31/713 |
| WO | WO-2015089419 A9 * | 11/2015 | ............. | A61K 48/00 |

OTHER PUBLICATIONS

Hyun-Jong Cho et al. "Poly-L-arginine and Dextran Sulfate-Based Nanocomplex for Epidermal Growth Factor Receptor (EGFR) siRNA Delivery: Its Application for Head and Neck Cancer Treatment." Pharmaceutical Research, vol. 29, 2012, pp. 1007-1019 and 3 pages of supplemental information. (Year: 2012).*

Dmitry G. Shchukin, Amish A. Patel, Gleb B. Sukhorukov, and Yuri M. Lvov. "Nanoassembly of Biodegradable Microcapsules for DNA Encasing." Journal of the American Chemical Society, vol. 126, 2004, pp. 3374-3375. (Year: 2004).*

J.F. Correia-Pinto, Mercedes Peleteiro, N. Csaba, Africa Gonzalez-Fernandez, M.J. Alonso. "Multi-enveloping of particulated antigens with biopolymers and immunostimulant polynucleotides." Journal of Drug Delivery Science and Technology, vol. 30, 2015, pp. 424-434. (Year: 2015).*

Akihiro Kishimura. "Development of polyion complex vesicles (PICsomes) from block copolymers for biomedical applications." Polymer Journal (2013) 45, 892-897. (Year: 2013).*

Edwin Donath et al., "Novel Hollow Polymer Shells by Colloid-Templated Assembly of Polyelectrolytes", Angewandte Chemie International Edition, 1998, 37(16): 2202-2205.

Masayoshi Fuji et al., "Shape-Controlled Hollow Silica Nanoparticles Synthesized by an Inorganic Particle Template Method", Advanced Powder Technology, 2012, 23: 562-565.

A.Gulbake and S.K. Jain, *Chitosan: a potential polymer for colon-specific drug delivery system*. Expert Opin Drug Deliv, 2012, 9(6): 713-29. (Abstract Only).

P. Huang et al., *Nano-, micro-, and macroscale drug delivery systems for cancer immunotherapy*. Acta Biomater, 2019, 85: 1-26.

Mitali Kakran et al., "Layered Polymeric Capsules Inhibiting the Activity of RNases for Intracellular Delivery of Messenger RNA", Journal of Materials Chemistry B, Jan. 1, 2015, 3(28); 5842-5848.

Denis Y Logunov, D., et al., *Safety and efficacy of an rAd26 and rAd5 vector-based heterologous prime-boost COVID-19 vaccine: an interim analysis of a randomised controlled phase 3 trial in Russia*. The Lancet , 2020, 396: 887-897.

D. Luo and W.M. Saltzman, *Synthetic DNA delivery systems*. Nat Biotechnol, 2000, 18(1): 33-7. (Abstract Only).

S. B. Manjila et al., *Novel gene delivery systems*. Int J Pharm Investig, 2013, 3(1): 1-7.

Anton M. Pavlov et al., "Location of Molecules in Layer-By-Layer Assembled Microcapsules Influences Activity, Cell Delivery and Susceptibility to Enzyme Degradation", *Journal of Controlled Release*, Aug. 14, 2013, 172(1): 22-29.

Y.K. Sung and S.W. Kim, *Recent advances in the development of gene delivery systems*. Biomater Res, 2019. 23: 8.

Y. Tarakanchikova et al., *Biodegradable Nanocarriers Resembling Extracellular Vesicles Deliver Genetic Material with the Highest Efficiency to Various Cell Types*. Small, 2020, 16(3): e1904880.

Alexander S. Timin et al., "Multi-Layer Microcapsules: Fresh Insights and New Applications", *Expert Opinion on Drug Delivery*, May 4, 2017, 14(5): 583-587 (May 4, 2017).

Alexander S. Timin et al., *Safe and Effective Delivery of Antitumor Drug Using Mesenchymal Stem Cells Impregnated with Submicron Carriers*. ACS Appl Mater Interfaces, 2019, 11(14): 13091-13104. (Abstract Only).

Jie-Xin Wang et al., "Direct Encapsulation of Water-Soluble Drug Into Silica Microcapsules for Sustained Release Applications", *Materials Research Bulletin*, 2008, 43: 3374-3381.

M.V. Zyuzin et al., *Multilayer Capsules Inside Biological Systems: State-of-the-Art and Open Challenges*. Langmuir, 2019, 35(13): 4747-4762. (Abstract Only).

* cited by examiner

BIODEGRADABLE MULTILAYER NANOCAPSULES FOR THE DELIVERY OF BIOLOGICALLY ACTIVE AGENTS IN TARGET CELLS

PRIORITY

This application is a continuation of U.S. application Ser. No. 16/634,060 filed Jan. 24, 2020, now U.S. Pat. No. 11,253,482 issued Feb. 22, 2022, which, in turn, corresponds to the U.S. National phase of International Application No. PCT/EP2018/070111, filed Jul. 25, 2018, which, in turn, claims priority to European Patent Application No. 17.183188.6 filed Jul. 26, 2017, the contents of which are incorporated by reference herein in their entirety.

SEQUENCE LISTING

The instant application contains a Sequence Listing that has been submitted in ASCII format via EFS-Web and is hereby incorporated by reference in its entirety. Said ASCII copy, created on Apr. 18, 2022, is named LNK_207D1_SEQ_LIST.txt and is 672 bytes in size.

BACKGROUND OF THE PRESENT INVENTION

One of the rapidly developing directions of biomedical research and nanotechnology is the design of new delivery systems for bioactive materials and, in particular, of genetic material into target cells. Various synthetic approaches for transfer of coding DNA and regulatory RNA molecules, e.g. short interfering RNA, non-coding RNAs and newly developed CRISP/Cas9 DNA and RNA elements to target cells have meanwhile been demonstrated. Most cancer cell lines can be efficiently manipulated with the help of these systems. However, establishment of the transfer of regulation elements to primary cells and embryonic or adult stem cells is time consuming and frequently accompanied by unwanted side effects hampering translation of in vitro findings to in vivo models and clinical practice.

For basic research purposes, efficient nontoxic approaches for manipulation of gene expression by knocking down a gene of interest using siRNA and miRNA, or overexpressing a gene of interest by transfer of coding DNA are sought. Whereas the majority of the established immortalized cells lines broadly used by the scientific community allow efficient RNA and DNA transfer using lipid-, polysaccharide-, polymer-, or calcium precipitation-based commercially available reagents, manipulation of gene expression in primary and stem cells remains a challenge. More complexity is expected by the establishment of targeted delivery in animal models and by translation of this technique to clinical practice, since further aspects have to be considered such as a promising drug delivery tool, e.g. regulated duration of substance release, cost-effectiveness and biocompatibility.

Mesenchymal stem cells (MSCs) have emerged as potential vehicles for gene transfer and delivery that together with other cells of the bone marrow, e.g. hematopoietic stem cells, serve as a tool for treatment of different diseases. Especially, MSCs have attracted attention among researches due to their ability to differentiate to various lineages including osteogenic, chondrogenic, neurogenic and adipogenic lineages, and for their ability to exhibit tropism to injured tissues and regulate the proliferation of immune cells. Thus MSCs are applied in regenerative medicine and as immune modulators, respectively. Consequently, manipulation of MSC properties by gene transfer and their application as gene carriers is an attractive opportunity for targeted gene therapy. However, low transfection efficiency and unwanted side effects encountered during viral transduction, e.g. integration of viral genome into the host DNA, hamper their broad application in clinical practice. Mesenchymal stem cells may therefore serve as a model for other types like primary cells, immune cells, tumor cells or embryonic stem cells.

Gao et al., Applied Materials & Interfaces, 2016, 8, 9651-9661, disclose intracellularly biodegradable polyelectrolyte/silica composite microcapsules where by a poly-L-arginine hydrochloride/dextran sulfate/silica composite capsule is formed and the inorganic $SiO_2$ composite capsule enables loading of small model molecules.

Timin et al., Scientific Reports, 2017, 7: 102 describe the preparation of $SiO_2$ coated hybrid capsules for efficient intracellular delivery of siRNA against influenza A virus infection.

Timin et al., Expert Opinion on Drug Delivery, 2017, Vol. 14, No. 5, pp 583-587 disclose multi-layer microcapsules having a diameter of 3-4 µm whereby the surface is coated with graphene oxide or $SiO_2$. The $SiO_2$ coated capsules show the formation of hollow structures of composite capsules with a shell thickness of about 100 nm.

EP 1 867 325 discloses capsules with a polyelectrolyte shell comprising a plurality of polyelectrolyte layers having a diameter of up to 10 µm whereby the shell contains certain lipids. The capsules contain different materials like macromolecules enclosed within a thin wall which is permeable for ions and small molecules.

Pavlov et al., Journal of Controlled Release (2013), pp. 22-29 disclose layer-by-layer assembled microcapsules wherein luciferase was used as monitor molecule.

Kakran et al., J. Mater. Chem. B (2015), pp. 5842-5848 describe layered polymeric capsules inhibiting the activity of RNases for intracellular delivery of messenger RNA.

FIELD OF THE PRESENT INVENTION

Being a natural communication system between the cells, extracellular vesicles (EV), have great potential as an approach for targeted delivery. The main advantages of naturally produced EVs compared with other common carriers, e.g. lipid-based nanoparticles, is their high penetration ability, delivery efficiency and biocompatibility. However, because they possess low loading efficacy, especially for RNA molecules, and because manipulation of naturally produced EVs as well as production of biomimetic nanovesicles is time- and cost-intensive, alternative carriers sharing the biomechanical properties of natural vesicles and the loading capacity of synthetic carriers can be an attractive alternative. Thus, there is a strong demand for bio-inspiring delivery system, such as EVs in terms of compatibility, cell uptake, size and regulated release to explore alternatives for RNA and DNA delivery.

SUMMARY OF THE PRESENT INVENTION

The biodegradable multilayer nanocapsules according to the present invention are of high similarity with the extracellular vesicles with regard to the size of single particle. In general the diameter of a nanocapsule ranges from 200-600 nm, preferably from about 60 nm to about 280 nm, or dependent on the preparation routine of CaCO3 core.

Polyelectrolyte capsules have been developed as a potent drug delivery system. For some applications porous micron and submicron sized $CaCO_3$ particles have been used as biocompatible templates with appropriate chemical and mechanical stability, and flexible structural parameters, allowing efficient incorporation of various payloads. Whereas formation of such particles and the kinetics of their mechanisms of crystallization are well studied, their loading methods with nucleic acids remain largely unexplored. In particular, loading of RNA molecules, e.g. siRNA, miRNA, sgRNA are of particular importance, since these molecules are highly susceptible to degradation and therefore need protection during storage and cellular delivery.

In one embodiment $CaCO_3$ particles have been adopted as a template to produce polyelectrolyte capsules using Layer-by-Layer (LbL) technique. Being based on electrostatic interactions of charged species positioned on neighboring layers and their alternating adsorption, LbL, has an unequalled degree of multifunctionality, which is important for delivery systems. The capsule formulation protocols, allow to tailor the surface with a variety of functional groups by incorporating polymers, lipids, and nanoparticles. By application of biocompatible and biodegradable chemicals, biodegradable polyelectrolyte capsules have been developed as attractive carrier for targeting intracellular molecules, and have been successfully tested in various in vitro models for transfer of drugs and RNA.

In this application, the preparation and the use of soft polyelectrolyte nanocapsules (about 200-600 nm, preferably from about 60-280 nm), whose biomechanical properties resemble those of extracellular vesicles, as a universal highly efficient approach for RNA transfer and specific regulation of gene expression is disclosed. As a model, cancer and mesenchymal stem cells were used and transfer of pro-apoptotic siRNA and anti-GFP siRNA for quantitative analysis and demonstration of the general principle of the approach.

Transfer efficiency and knockdown effect was compared with commercially available transfection reagents commonly used for siRNA-based knockdown in vitro, looking also at intracellular trafficking and degradation of internalized capsules. It is essential that these data were obtained in vitro before paving the way for further in vivo research on polyelectrolyte nanocapsules as a universal platform for efficient transfer of any type of oligonucleotides, including non-coding miRNAs, IgRNA, sgRNA, DNA, drugs and proteins in various in vivo systems.

The present invention provides biodegradable multilayer nanocapsules for the delivery of at least one biologically active agent into at least one target cell consisting of at least two layers of at least two biodegradable polymers which are laid one onto the other and whereby the biologically active agent is layered onto a layer of a biodegradable polymer and covered with a further layer of a biodegradable polymer. Consequently the biologically active agent is preferably between two layers of biodegradable polymers whereby the biodegradable polymers may be the same or different. The biologically active agent can be different in the single layers. It is possible to include 2, 3 or even more different DNA or RNA layers which may have different size in the single layers.

In a preferred embodiment of the present invention the biodegradable multilayer nanocapsule is present as a core-free capsule. For the production of the nanocapsule it is, however, advantageous to use first a core onto which the layers of the biodegradable polymer(s) are laid. In a particularly preferred embodiment as core small particles having a well-defined low diameter of $CaCO_3$ are used. After the degradable polymers and the biologically active agent have been layered onto the particle, the core can be dissolved. In preferred embodiments the core is made from $CaCO_3$, but also other particles like sugar pareilles can be used. When sugar particles are used as core it is possible to dissolve the sugar core by reducing the concentration of the sugar in the reaction mixture.

In a preferred embodiment of the present invention the nanocapsule is core-free. When the core consisting e.g. of $CaCO_3$ is dissolved at the end of the process, the centre of the capsule is void.

In another embodiment, when two different biologically active agents are intended to be delivered to the target cell, it is possible to include one biologically active agent in the core by simply adding the agent to the solution from which the core particles are formed. When the core contained a biologically active agent and the core is dissolved after the surrounding layers have been formed, this biologically active agent is trapped within the shell formed by the biodegradable polymers which comprise the second biological agent. In this way two different biologically active agents can be efficiently transported into the target cell whereby first the biological agent which is trapped between the layers of the biodegradable polymers is liberated and after the whole shell has been dissolved the second biologically active agent which is trapped within the shell is set free.

In order to ensure an efficient uptake of the nanocapsule by the target cells it is of utmost importance that the diameters are in a well-defined range. Depending on the target cells the diameter of a single nanocapsule ranges from about 60 to about 800 nm, whereby a range of 60 nm to 600 nm is preferred and a range between 60 nm and 200 nm is particularly preferred for primary stem- and immune cells. The core is covered with at least one layer of a biodegradable polymer. As biodegradable polymers, such polymers can be used which are dissolvable in the target cells after the nanocapsule has found its way into the target cells. It is also preferred that the biodegradable polymer has an electric charge depending on the pH value of the environment. Preferred examples of biodegradable polymers are dextran sulfate which is preferably present as sodium salt or poly-L-arginine which is preferably present as hydrochloride. Onto the biodegradable polymer the biologically active agent is applied which may again be covered with the same or a different biodegradable polymer.

In a preferred embodiment multiple electrostatic layers are deposited on the core particle using a layer-by-layer (LbL) approach. In a preferred embodiment successive and alternating anionic and cationic layers are added to the core. After the addition of each polyelectrolyte there is usually a wash and centrifugation step.

The advantage of the biodegradable polymer is the electric charge which helps to strengthen the binding between the biodegradable polymer and the biologically active agent in view of the opposite electric charge.

The biologically active agent which is transported into the target cell with the help of the nanocapsule is preferably a nucleic acid. Such nucleic acids may be selected from RNA, siRNA, mRNA or DNA. It is, however, also possible to transport proteins or peptides into the target cell. When for example the target cell is an immune cell like a T cell the peptide may comprise an epitope against which antibodies shall be formed.

In another embodiment it is, however, also possible to encapsulate RNAs together with a protein. It is particularly preferred to encapsulate the RNAs with a Cas9 protein and the desired gRNA either simultaneously or successively. Two embodiments are possible. In the first embodiment the appropriate Cas9 protein is entrapped in one set of nanocapsules and the gRNA is entrapped in another set of nanocapsules. The two nanocapsule fractions are mixed in an appropriate ratio preferably in a range of about 1:1 and this mixture is used for transferring/transfecting the target cells. When the gRNA is used, specific care has to be taken in order to avoid the presence of RNases in order to avoid an undesired degradation of the gRNA.

When, however, in the second embodiment the gRNA and the Cas9 protein are applied together it is assumed that the gRNA is protected (e.g. wrapped in a Cas9 protein) which avoids a degradation of the nucleic acid. A further advantage of using gRNA and the appropriate Cas9 protein together is that the complex can move directly into the nucleus and start with the action of modifying the target DNA.

When in a further embodiment the Cas9 protein is entrapped in the nanoparticle in the form of an mRNA sequence the protein has to be translated first and after translation the gRNA has to meet the Cas9 protein. Such difficulties have to be overcome by precisely calculating the appropriate amounts of the active components.

Therefore, the embodiment wherein gRNA and Cas9 protein are entrapped within the nanocapsules as RNP complexes is preferred. The RNP complexes should be negatively charged. This improves the loading into the nanocapsules.

In a particularly preferred embodiment the nanocapsules of the present invention comprise therefore as biologically active agent a suitable nucleic acid and a corresponding protein. The RNP complex of a Cas9 protein and a suitable gRNA are particularly preferred.

The present invention provides also a process for the preparation of biodegradable multilayer nanocapsules which comprises the following steps:

First, a core which may consist of $CaCO_3$ or of a sugar pareille may be prepared by processes known in the art. It is essential that the size of the particles is very well defined and that the single particles have a uniform distribution of diameters. A classification of the size of the core particles may be required.

Then the core particles are coated with a first layer of a biodegradable polymer. Together with the first layer a dye, e.g. a fluorescent dye, with a corresponding charge can be added, if visualization of capsules is desired. It is possible to apply several layers of biodegradable polymer which may be different from each other. Depending on the selected process washing steps between the single coating steps may be required.

Then the biologically active agent is brought into contact with the biodegradable polymer whereby opposite electric charges improve the binding and result in an efficient loading of the particle. It may be sufficient when the particles coated with one or more biodegradable polymer layers are stirred in a suitable solution wherein the biologically active agent is dissolved. As consequence of opposite electric charges the biologically active agent will adhere efficiently to the biodegradable polymer.

Then a further coating layer of a biodegradable polymer can be applied. Excess of reagents is removed from the reaction mixture, for example by centrifugation and washing.

Finally the core is removed from the nanocapsule by dissolving the core. When the core of the nanocapsule is formed from $CaCO_3$, removal of the core may be obtained by a complexing agent like ethylene diamine tetraacetic acid (EDTA). In this step the calcium ions are complexed and the calcium carbonate is dissolved. This may be supported by slightly lowering the pH value of the solution.

Optionally it may be possible to include a step for providing a homogenous distribution of size of the nanocapsules by passing the nanocapsules through several filters with appropriate size. Alternatively the nanocapsules are forced to go through a microfluidic channel system which allows a sorting according to the size.

The nanocapsules of the present invention are preferably used for the efficient uptake of the biologically active agent into a target cell. To improve the specificity of the nanocapsule it is also possible to include specific compounds which increase the efficiency of uptake into certain cells. This may be in particular advantageous when the nanocapsules are applied to patients, for example by injection. The specificity of the nanocapsules can be improved for example by coupling specific ligands to the nanocapsules which bind to receptors of the target cells.

An object of the present invention is the specific and efficient delivery of genetic material which is one of the main challenges in molecular medicine today. While extracellular vesicles function as natural nanocarriers, the soft biodegradable polyelectrolyte nanocaspules presented here can be employed as universal artificial nanovehicles with similar biomechanical properties. Using functional siRNA molecules as a model, it has been demonstrated that an alternative loading technique achieved by incorporating RNA between the layers allows consecutive release during capsule degradation within the cell and a sustainable knockdown effect of a corresponding target gene. Additionally, simultaneous loading with several different payloads incorporated between different layers can be employed. Cell uptake, duration of biodegradation on the nanocapsules and their impact on cell viability were tested both in cancer and mesenchymal stem cells. Near to 100% transfer and knockdown efficiency was demonstrated using only $2.5 \times 10^{-4}$ pmol siRNA/20 capsules/cell, which is several magnitude orders below the amount of RNA required for any of the microcapsule-, lipid-, and polymer-based methods reported so far. This confirms biodegradable nanocapsules to be a universal, highly efficient and stable nanoscale platform for transfer of genetic material.

The biodegradable multilayer nanocapsules of the present invention have several advantages. It is possible to introduce molecules into target cells in a simple, reliable and specific way. It has been found that without toxic side effects the uptake of about 10 to 20 biodegradable multilayer nanocapsules/cell is possible. Without wishing to be bound to a theory it is assumed that the high uptake and transfection efficiency is due to the preferred size of the nanocapsules which resemble small extracellular vesicles, e.g. exosomes and exosome-like vesicles known naturally transfer functional genetic material, e.g. mRNA and miRNAs. Therefore, the nanocapsules can be transported into the cells by using transport mechanisms which are present on the target cells and which are highly specific and very efficient. Another advantage of the present nanocapsules is that the core is dissolved and that no silica ($SiO_2$) is present in the nanocapsule of the present invention. Furthermore, it is assumed that the use of the biodegradable polymer improves the availability of the biologically active agent in the target cells. Silica or other non-biodegradable polymers are preferably not part of the nanocapsules according to the present invention.

In recent years, different promising strategies for transport of regulatory RNAs, e.g. siRNA, miRNA, or CRISP/Cas sgRNA and DNA have been developed, employing transfer of RNA and DNA molecules with capsules, proteins, polymers or vesicles to target cells and organs. In this application, biodegradable nanocapsules are disclosed as a novel tool for simple protection and transportation of RNAs and other molecules. Furthermore as compared with available alternatives, the approach described here requires a lower amount of material and exhibits higher efficiency in uptake, delivery and functionality. Protocols for production of soft biodegradable polyelectrolyte nanocapsules of 200-600 nm and preferably from about 60 to about 280 nm were established which are considerably smaller than commonly used microcapsules of 3-5 μm diameter. Similar to conventional capsules, $CaCO_3$ was used as a core and surrounded by layers of the biodegradable substances dextran sulfate (DS) and poly-L-arginine hydrochloride (PARG) using the layer-by-layer (LbL) coating technique. As a technical novelty, apart from drastic reduction of capsule size, the positioning of the functional siRNA molecules between the layers enables their consecutive release during degradation within the cell, sustainable knockdown effect and loading with several different siRNA allowing simultaneous knockdown of several targets. Biocompatibility tests showed no cytotoxicity and no influence of capsules on viability or metabolic activity of the target cells when treated with more than 20 capsules per cell for cancer cells and MSCs, both cell lines demonstrated highly efficient uptake. Functional analysis of the loaded siRNA molecules revealed over 80% knockdown efficiency in any cell type tested, indicating target cell universality and exceptionally high efficiency of the developed approach.

It is assumed that the small size of the capsules allows their relocation to the perinuclear region and endocytic compartments, resembling the intracellular location of natural extracellular vesicles after uptake and subsequently allowing transfer of functional RNA molecules to physiological sites, which supports their functionality. Thus, the biocompatible polyelectrolyte nanocapsules are perfectly suited for delivery of nucleic acids to target cells. Due to the new technique of RNA loading between the PARG layers, it is possible that different payloads can be used simultaneously in nanocapsules, offering an additional advantage. Finally, the nanocapsules presented herein exhibited regulated consecutive siRNA release starting 12 h after treatment and completed after 48 h. Furthermore, the siRNA tested in this approach offers high potential for adaptation as a therapeutic delivery system for transfer of functional RNA and DNA: siRNA, miRNAs, sgRNA/Crisp and other to desired target cells in vitro and in vivo.

The data reported in the study envisage that the biodegradable nanocapsules will serve not only as an ultimate tool for nucleic acid transfer in in vitro systems, rather, that they can be implemented in the treatment of patients, where scheduled administration of a drug is required. Capsules exhibit clear advantages over common carrier systems in that they release their content directly after suspension while at the same time offering exceptional high stability by retaining active siRNA molecules for longer than a year.

The details of the present invention are further described in the Figures and the Examples of the present application, which disclose preferred embodiments of the invention.

BRIEF DESCRIPTION OF THE DRAWINGS

FIG. 1A shows SEM image of a vaterite $CaCO_3$ particle; FIG. 1B shows an SEM image of core-shell capsules showing spheroid structures of slightly different sizes. The size of capsules is directly dependent of the size of $CaCO_3$ valerites, which is determined by concentration of the reagents, salts solubility, reaction time, and rotation speed during mixing.

FIG. 2A shows a schematic representation of capsule loading with siRNA: first, two layers of DS and PARG are coated on the $CaCO_3$ core; then siRNA layer can be coated directly on a PARG and covered with an additional PARG layer. As the last step, core can be removed with EDTA; FIG. 2B shows images of capsules loaded with encapsulated Rhodamin B isocyanate (RdnB) and control siRNA, labeled with Alexa Fluor 488 (ctrsiRNA-488); RdnB/(DS/PARG)2/siRNA/PARG). In the red channel, Rhodamin B is visible, showing capsules loaded with RdnB; in the green channel Alexa Fluor 488 can be visualized. Overlay of both images shows a clear merge of both colors giving the color yellow, indicating successful encapsulation of siRNA into the capsules.

FIG. 3A shows that for determination of optimal capsule concentration 10, 20 and 50 capsules/cell were applied for treatment of HT1080 cells; 24 h post-treatment cells were fixed; stained with phalloidin-Alexa488 and DAPI and subjected to confocal microscopy. Only few capsules could be visualized by application of 10 capsules/cell; concentration of 20 capsules/cell was considered as optimal; whereas 50 capsules/cell exhibited toxic effect, causing nuclei deformation (white arrow heads) and access of not internalized capsules in the solution (white arrows). FIG. 3B shows a comparison of intracellular localization of nanocapsules (left image, showing uptake of capsules loaded with siRNA-Alexa488) and vesicles (right image, showing uptake of vesicles loaded with red dye PKH26). Very similar localization in the perinuclear region suggests that nanocapsules are able to deliver their payloads, e.g. RNA to physiological intracellular sites mimicking extracellular vesicles in their function. Scale bar 50 μm.

FIG. 4A shows that to examine degradation of capsules within the cells, HT1080 cells were treated with capsules loaded with RdnB and ctrsiRNA-488. Then 4, 24 and 48 h after treatment the cells were fixed, stained with phalloidin and DAPI and subjected to confocal microscopy (scale bar 30 μm). Yellow color on the images indicates merged RdnB and ctrsiRNA-488 signals (mostly visible after 4 h) and intact capsules. Appearance of red and green dots after 24 h indicates capsule degradation. FIG. 4B shows a quantitative analysis of capsule degradation. A black line (□) indicates intensity of yellow signal, showing that majority of capsules is intact; grey lines show intensity of yellow color after 24 (○) and 48 (Δ) h respectively, showing decrease of a number of intact capsules. FIG. 4C shows a diagram, showing decrease of a portion of the intact capsules from 100% after 4 hours to only 19% after 48 h. This reflects the efficient uptake of the nanocapsules.

FIG. 5A shows a confocal microscopy of the HT1080 cells treated with capsules loaded with GFP-specific siRNA or transfected with Lipofectamine 2000 using the same amount of siRNA/cell. As a control, unspecific ctrsiRNA-488 was used. Images were taken 48 h post treatment. FIG. 5B shows a plot diagram showing quantitative analysis of the knockdown efficiency extrapolated from the reduction of the GFP signal intensity. Image freeware was used for the analysis. FIG. 5C shows a diagram showing decrease of green fluorescence indicating 80% knockdown efficiency by capsules and only 21% by Lipofectamine application.

FIG. 6A shows confocal images of HT-1080 cells treated with capsules loaded with AllStar Cell Death Control siRNA inducing apoptosis (apoptsiRNA) or with a control siRNA. Images were taken 24 and 48 hours of incubation with capsules. In samples treated with the apoptosis-inducing RNA, nuclei deformation and condensation typical for apoptotic cells were observed (white arrows).

FIG. 6B shows a diagram showing results of WST-1 viability assay for quantification of apoptosis induced by capsules loaded with apoptsiRNA and either maintaining their core or core-free. Treatment of cells with Tween-20 was used as a positive control of cell death.

FIG. 7A shows confocal images of MSCs treated either with capsules loaded with apoptsiRNA and ctrsiRNA, or transfected with Lipofectamine 2000 using the same siRNAs. To control morphology of intact cells, images of untreated MSCs were taken. All cells were cultured for 48 h, fixed as stained with phalloidin-Alexa488 and DAPI prior microscopy. To control capsule stability, MSCs were treated with capsules stored for 1 year by 4° C. FIG. 7B shows that to quantify apoptosis, WST-1 assay was performed. Highly significant reduction of cell number was measured after application of fresh capsules and capsules stored for 1 year capsules after loaded with AllStar Cell Death siRNA, no significant reduction of cell viability could be detected upon transfection of corresponding amounts of siRNA with Lipofectamine 2000.

FIG. 8A shows that to control vesicle integrity, transmission electron microscopy was performed. Typical for exosomes and other extracellular vesicles, structures of 60-150 nm diameter exhibiting so-called "cap-like" shape which membrane vesicles may acquired during drying procedures, are detectable on the grid, indicating that intact vesicles were isolated from the cell culture supernatants. FIG. 8B shows that to calculate EV number and size distribution, NTA analysis was performed. $2.25 \times 10^9$ particle/ml was detected in the preparation.

FIG. 9A shows prior experiments with capsules, GFP expression was controlled by FACS analysis. 98.9% of the HT1080-GFP cells exhibited GFP expression, detected in the FL1 channel as a green fluorescence (red line). The parental HT1080 cells served as a negative control (black line). FIG. 9B shows that additionally, GFP expression was controlled by Western Blot analysis. GFP signal was detected in the HT1080-GFP cells, but not in the HT1080 cells. GAPDH served as a loading control.

FIGS. 12A-12C shows capsules for transfer of genetic material to tumor and primary cells differ in their size. FIG. 12A presents scanning electron microscopy images of capsules used for siRNA and mRNA transfer in tumor cell lines and primary tumor cells, showing $CaCO_3$ core (left panel) and the capsules after loading (right panel). FIG. 12B presents scanning electron microscopy images of smaller capsules used for transfer of genetic material to primary immune- and hematopoietic cells that were produced using a slightly modified protocol. $CaCO_3$ core (left panel) was coated with several layers of polymers (right panel).

FIG. 12C presents a nanoparticle tracking analysis showing nanocapsules with a size distribution between 50 and 280 nm

DETAILED DESCRIPTION OF THE PRESENT INVENTION

Particularly preferred embodiments of the present invention are shown in the following Examples:

Example 1

Figure 1A:
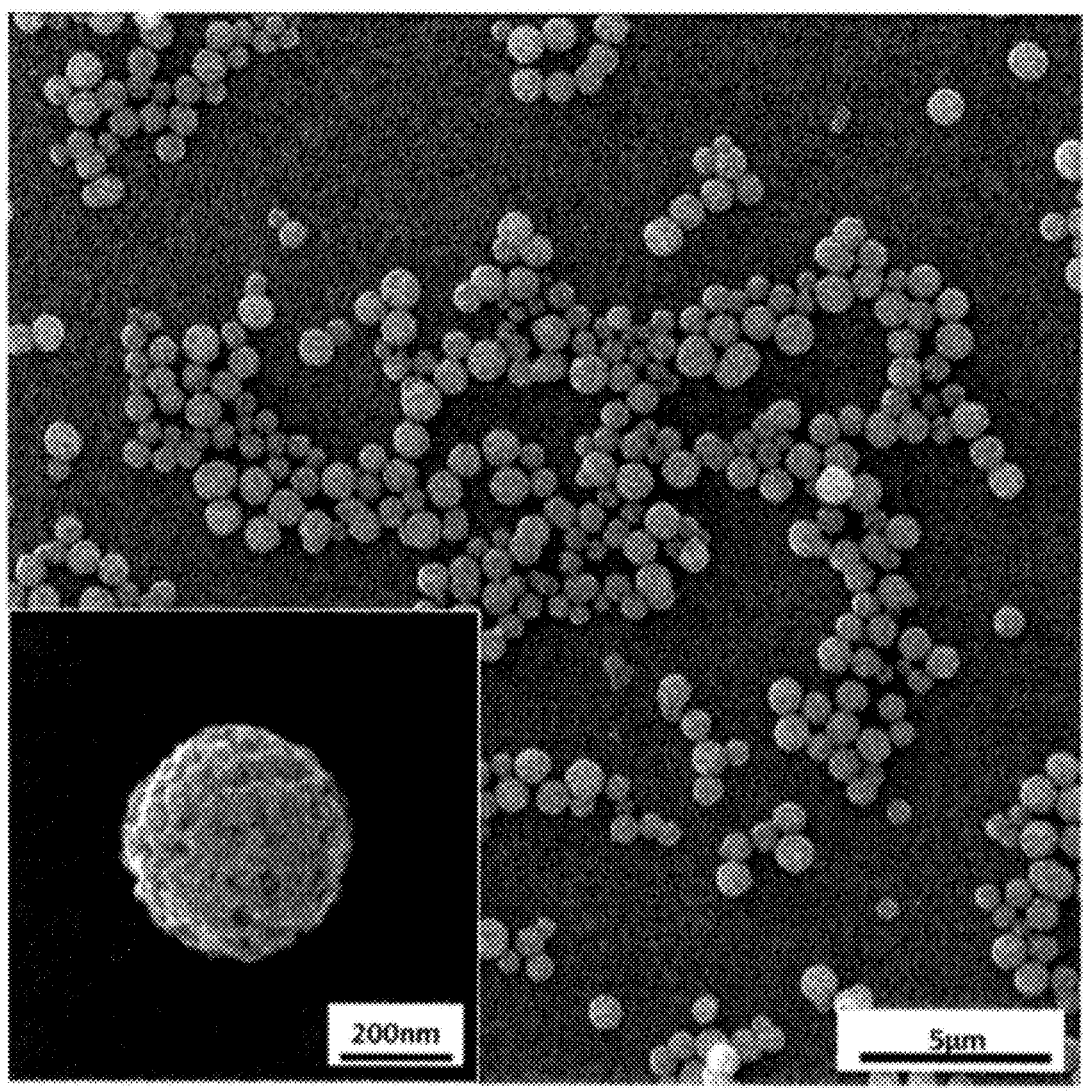
FIGS. 1A and 1B show a characterization of the capsules by scanning electron microscopy (SEM).
Figure 1B:
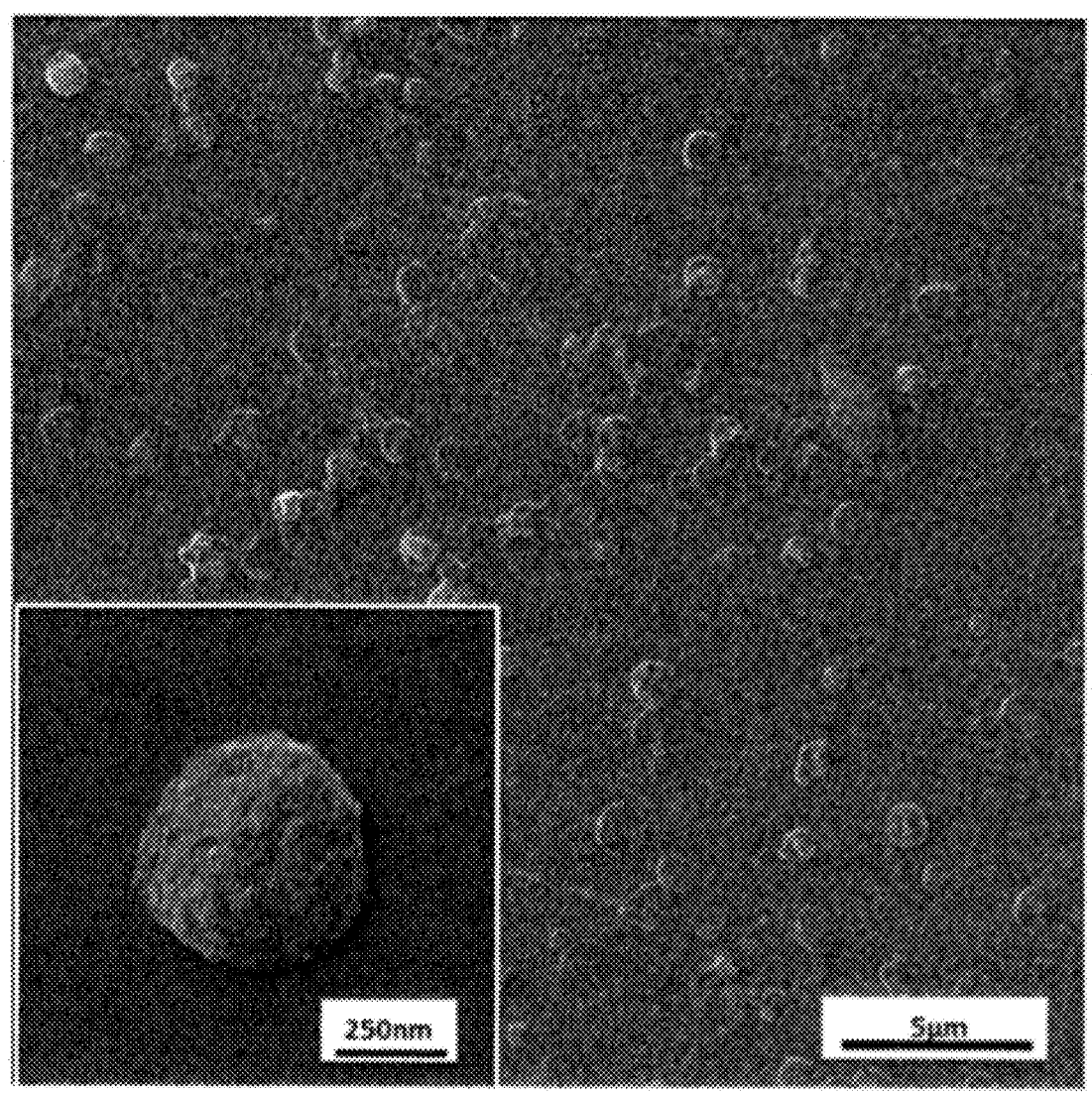

First, a new protocol allowing production of small biodegradable capsules with efficient encapsulation of high RNA amounts was established. The capsules are shown in FIGS. 1A and 1B. For this purpose, preparation of a $CaCO_3$ core was done using a recently developed protocol (FIG. 1A). Salt concentration and duration of stirring conditions were adjusted to produce particles 100-600 nm diameter (FIG. 1B). Then two biodegradable polymers, dextran sulfate sodium salt (DS) and poly-L-arginine hydrochloride (PARG), were assembled using LbL technique to produce biodegradable capsules.

The following materials were used: Anhydrous sodium carbonate, sodium chloride, ethylene glycol, calcium chloride, dextran sulfate sodium salt (DS, MW>70 000), poly-L-arginine hydrochloride (PARG, MW>70 000), Rhodamine B isothiocyanate (MW 536.08), phosphate buffered saline (PBS, 0.01M), calcium chloride dihydrate, ethylenediaminetetraacetic acid disodium salt (EDTA), dimethyl sulfoxide (DMSO), were all obtained from Sigma-Aldrich. RPMI-1640 medium, fetal bovine serum (FBS), was purchased from Thermo-Fischer Scientific. Control siRNA labeled with Alexa 488 (ctrsiRNA-488) and AllStar Death Control siRNA (apoptsiRNA) were purchased from Qiagen.

The capsules were prepared as follows: One ml of 0.33M $Na_2CO_3$ and 1 ml of 0.33M $CaCl_2$) were dissolved in 10 mL ethylene glycol (EG) and rapidly mixed under magnetic stirring for 3 h. The final size of the vaterite particles depends strongly on the concentration of the reagents, the solubility of the salts, the reaction time, and the rotation during mixing. The size of $CaCO_3$ was obtained in the range of 100-600 nm. After 3 h of stirring, the particles were sedimented by centrifugation, resuspended in 1 ml of dd$H_2O$ and stored at 4° C. until further use.

Example 2

Loading of Core Particles

To demonstrate their applicability for regulation of gene expression and their efficiency, the transfer of siRNA molecules into the cells a test model was used. For quantitative analysis of RNA incorporation and release, RNA labeled with AlexaFluor488 dye (ctrsiRNA-488) was applied. Additionally, an external cationic dye, Rhodamine B isothiocyanate (RdnB) conjugated with polymer PARG, was chosen for visualization of capsules by confocal microscopy. To allow simultaneous loading of different payloads and a controlled consecutive siRNA release, a new encapsulation method was developed. The RdnB dye served as a first layer if labeling of capsules was desired, followed by 4 alternating DS and PARG layers.

Figure 2A:
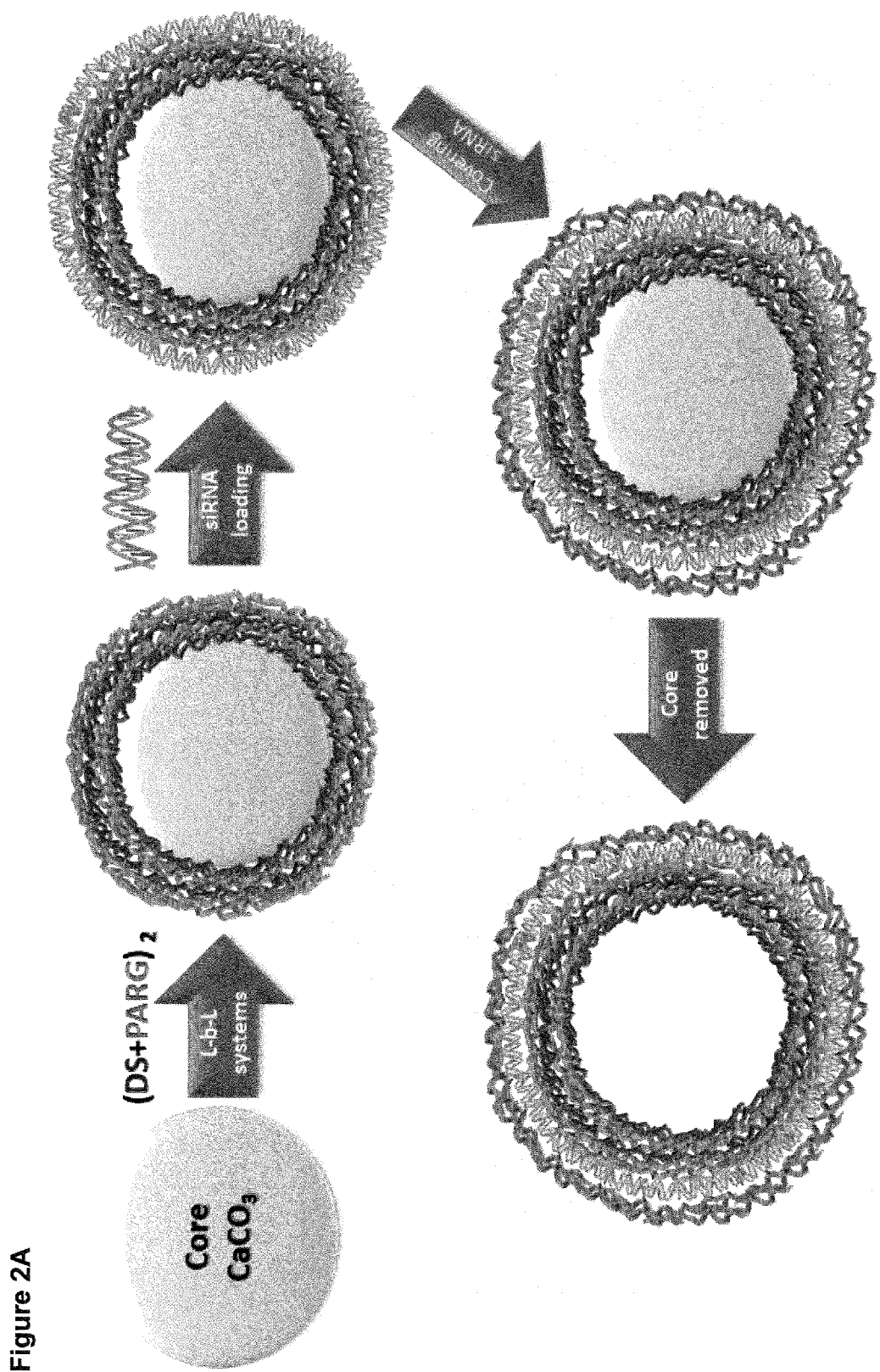
FIGS. 2A and 2B show the preparation of nanocapsules loaded with a fluorescent dye and siRNA.
Figure 2B:
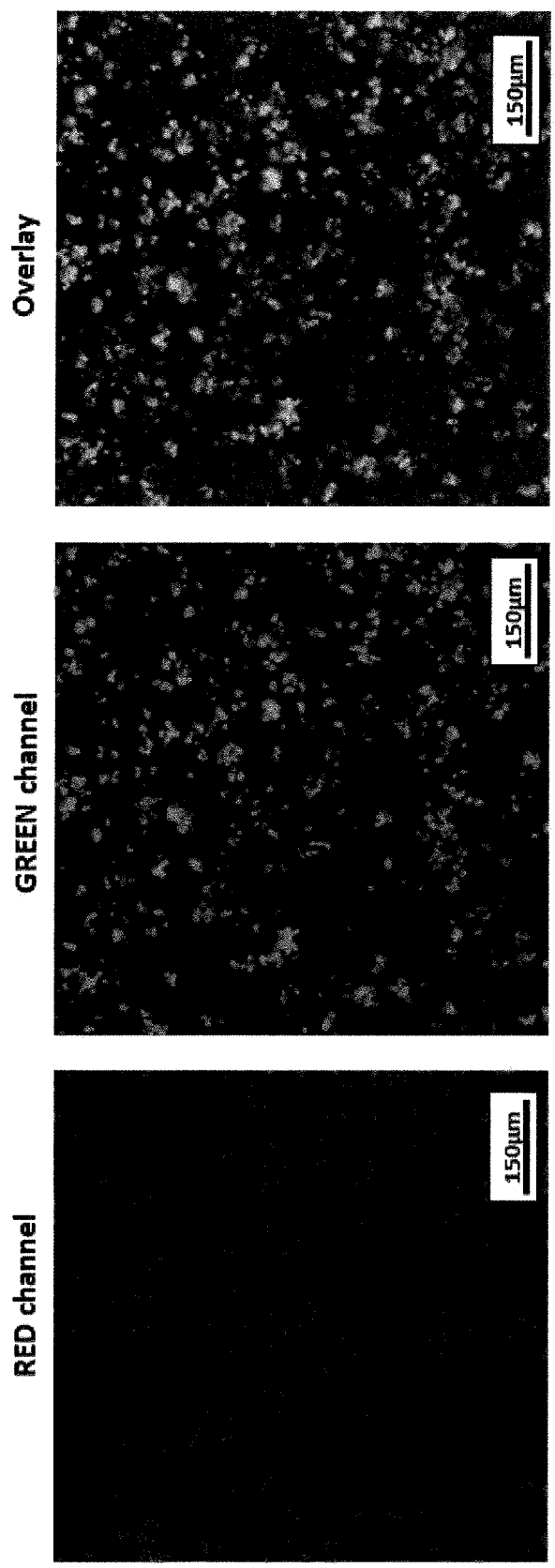

Employing electrostatic interactions between positively charged PARG and negatively charged oligonucleotides; siRNA was positioned between 2 PARG layers as shown in FIG. 2A. As the last step of capsule preparation, $CaCO_3$ core was removed with EDTA (FIG. 2A). Imaging of siRNA-containing capsules labeled with RdnB showed a complete overlay between siRNA-Alexa488 (green channel) and RdnB (red channel), indicating highly efficient incorporation of siRNA into the capsules (FIG. 2B). Measurement of RNA concentration revealed 1.25 pmol siRNA/$1 \times 10^6$ capsules.

RNA and dye encapsulation. Encapsulation of a dye was developed using the layer-by-layer (LbL) technique. The LbL technique is based on the sequential adsorption of oppositely charged molecules, such as polyelectrolytes, onto a charged sacrificial template. For the layers biocompatible polyelectrolytes Dextran Sulfate (DS) 1 mg/ml (2 ml) and Poly-L-arginine hydrochloride (PARG) 1 mg/ml (1 ml) were applied. For preparation of labeled capsules, rhodamine isocyanate (concentration 1 mg/ml) was added as a first layer to $CaCO_3$ particles diluted in 2 mL of dd$H_2O$ which was conjugates with polymer PARG. Then 2 layers of DS and PARG were coated consequently.

For encapsulation of siRNA a new method was developed. First, 50 µl of the 20 pmol siRNA solution was diluted in 1 ml RNAse-free, DNase-free dd$H_2O$. Next, the siRNA layers were coated on the PARG layer and covered again with a PARG layer. It is important that the last layer has a positive charge. Next, the core was removed with Ethylenediaminetetraacetic acid (EDTA); capsules were resuspended in 1 ml dd$H_2O$ and final concentration $8 \times 10^8$/ml.

The key advantages of the method of the present invention include:
1) highly efficient incorporation of oligonucleotides from the starting solution into the final formulation with more than 90% of the capsules covered with RNA;
2) quantitative loading of oligonucleotides/capsule;
3) a unique possibility to simultaneously use several payloads under controlled conditions, e.g. a drug, filling a $CaCO_3$ core using a conventional technique, different nucleic acid layers positioned between PARG layers, and functional groups positioned on the top layer, e.g. peptides, ligands, polysaccharides or nanoparticles.

Example 3

Uptake Efficiency and Delivery to Physiological Intercellular Sites

Figure 3A:
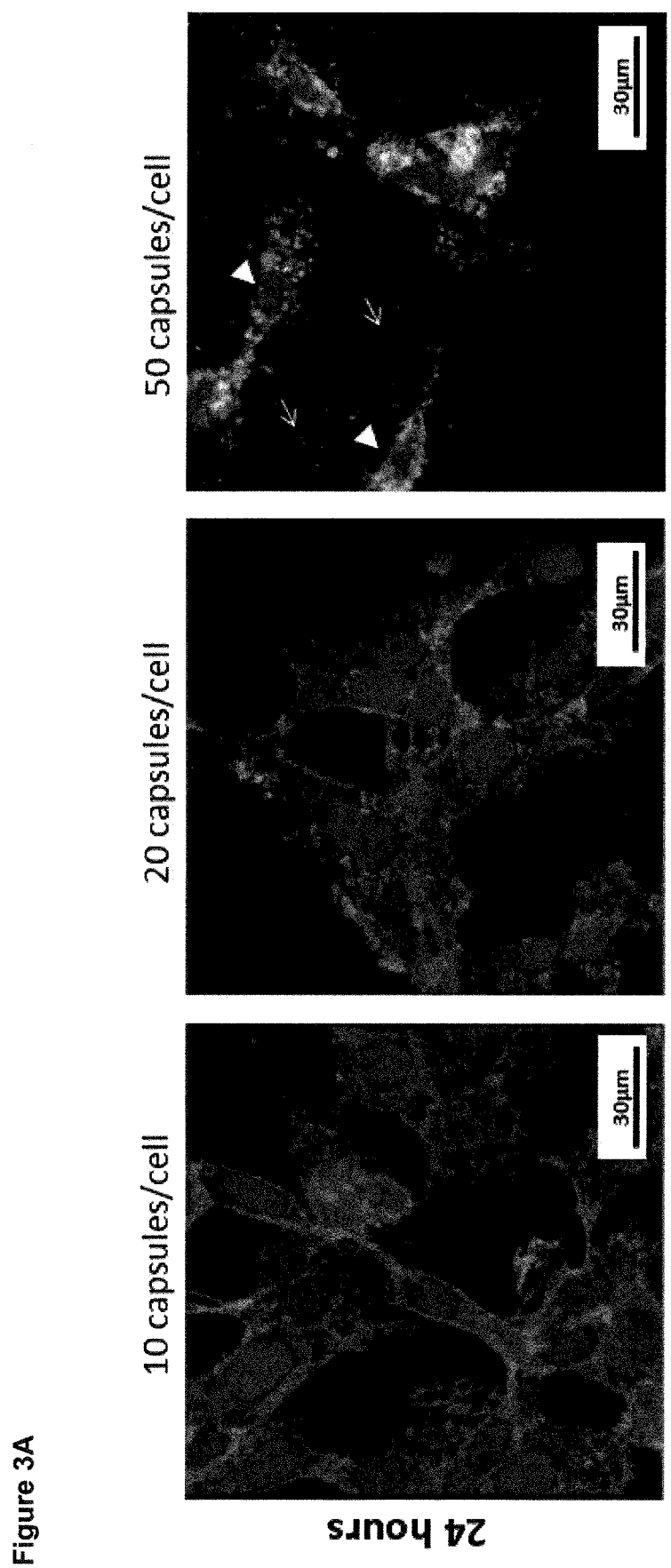
FIGS. 3A and 3B show the efficient uptake and intracellular localization of polyelectrolyte nanocapsules in HT1080 cells.

The uptake efficiency of capsules using HT1080 fibrosarcoma cells as a model was assessed. For estimation of a potential impact of capsules on cell viability, confocal microscopy was employed, monitoring nuclear morphology by staining with DAPI and building actin stress fibers by staining the actin filaments with phalloidin. The uptake efficiency was tested using different capsule concentrations: 10 capsules/cell, 20 capsules/cell and 50 capsules/cell. Capsules labeled with RdnB were used for their intracellular visualization; confocal images were taken 18 h after capsules were added to the cell culture medium. By application of 10 and 20 capsules/cell, no residual capsules were detected in the cell culture medium, indicating high uptake efficiency. No evidence of stress fibers or deformation of nuclei indicating toxic effects were observed (FIG. 3A left and middle panels). In contrast, application of 50 capsules/cell resulted in deformation of cell and nuclear shapes (FIG. 3A, right panel, arrow heads), indicating toxic effects as described elsewhere; furthermore, a number of capsules remained in the cell culture medium (FIG. 3A, right panel, arrows).

Cells culture and viability assay. HT-1080 and HT1080-GFP cells were cultured in RPMI-1640 medium supplemented with 10% heat-inactivated Fetal Bovine Serum (FBS). To measure cytotoxicity and viability, WST-1 assay was performed according to the manufacturers recommendations. Briefly, cells were seeded in a 96-well plate and incubated overnight. After administration of capsules loaded with corresponding siRNAs or treated with Tween-20 used as a positive control for cell death, cells were cultured for 24, 48 or 72 h, respectively as required. WST1 reagent was added to each well and maintained for 4 h. Optical density was measured using TECAN Elisa Reader.

siRNA Transfer by Capsules and Transfection

One day before transfection or treatment with capsules, HT1080 and HT1080-GFP cells were seeded in 4-well or 8-well chamber slides (Ibidi) using $2 \times 10^4$ cells in 300 µL of cell culture medium per well and grown overnight to the expected cell density of 60-70%. Capsules were added at concentration 20 capsules/cell and incubated for the desired duration. For transfection Lipofectamine 2000 was used; transfection was performed according to the recommendation of the supplier. Cells were transfected with an amount of siRNA, corresponding to the amount of siRNA loaded in the capsules. Thus, $1.6 \times 10^6$ capsules and 20 pmol siRNA were used for $8 \times 10^4$ cells for treatment or transfection respectively.

In pursuing the main goal of developing a carrier system mimicking natural extracellular vesicles containing functional RNA, e.g. exosomes or microvesicles, it is assumed that if capsules resembled them, the same intracellular traffic routes to deliver encapsulated RNA to the corresponding physiological intracellular commitment sites are used. To prove this, extracellular vesicles from cancer cell supernatants were isolated by conventional ultracentrifugation, allowing enrichment of exosomes as follows:

Isolation of Cell Culture Derived Extracellular Vesicles

Fibrosarcoma HT1080 cells were cultured in RPMI+10% FBS at 37° C. and 5% $CO_2$. 36 h prior to harvesting the vesicles produced, medium was changed to serum-free RPMI. Harvested medium was centrifuged for 15 min at 2,000×g, followed by 45 min at 5,000×g and 30 min at 12,000×g. The supernatant was filtered with a 0.2 μm membrane and concentrated in a concentration chamber to achieve a volume of 30 to 50 ml. This concentrated supernatant was centrifuged at 120,000×g for 1.5 h. The resulting supernatant was discarded and the exosome pellet washed with 11.5 ml Sodium Chloride, followed by a second centrifugation step at 120,000×g for 2 h. The supernatant was discarded and the exosome pellet resuspended with sodium chloride with a final volume of 200 μl per cell line.

Transmission Electron Microscopy

The quality of exosomes was controlled by Transmission electron microscopy (TEM). 10 μl of the vesicle preparation were loaded on a 300-mesh copper grid and fixed with 1% glutaraldehyde. Next, they were washed with double distilled water and negatively stained with 10 μl drop of 1% uranyl acetate and washed. Images were taken by the electron microscope (LEO 906 E, Zeiss, Oberkochen, Germany) using SIS software (Olympus, Hamburg, Germany)

Nanoparticle Tracking Analysis

Exosome and Capsule concentration and size distribution were analyzed by nanoparticle tracking analysis (NTA) using the ZetaView system PMX110 (Particle Metrix, Meerbusch, Germany) according to the manufacturer's instructions. Briefly, samples were diluted in filter-sterilized HEPES buffers; using ration 1:500 for exosomes and 1:100 for capsules. Images were recorded at 11 positions and 5 cycles with camera sensitivity 95%; shutter position 70; temperature was monitored manually, ranged from 21 to 22° C.

Staining of Vesicles with PKH26

Staining of vesicles with PKH26 (Sigma-Aldrich) was performed. Briefly, vesicle pellets after ultracentrifugation were resuspend in 200 μl PBS. Then 500 μl of Diluent C provided by the supplier was added to the solution and mixed with 1 μl of PKH dye diluted in 500 μl diluent C. Vesicles in a final volume of 1.2 ml were incubated for 5 min, washed. Remaining dye was removed by centrifugation in 100 kDa centrifugal filter unit (Amicon, Sigma-Aldrich).

Figure 3B:
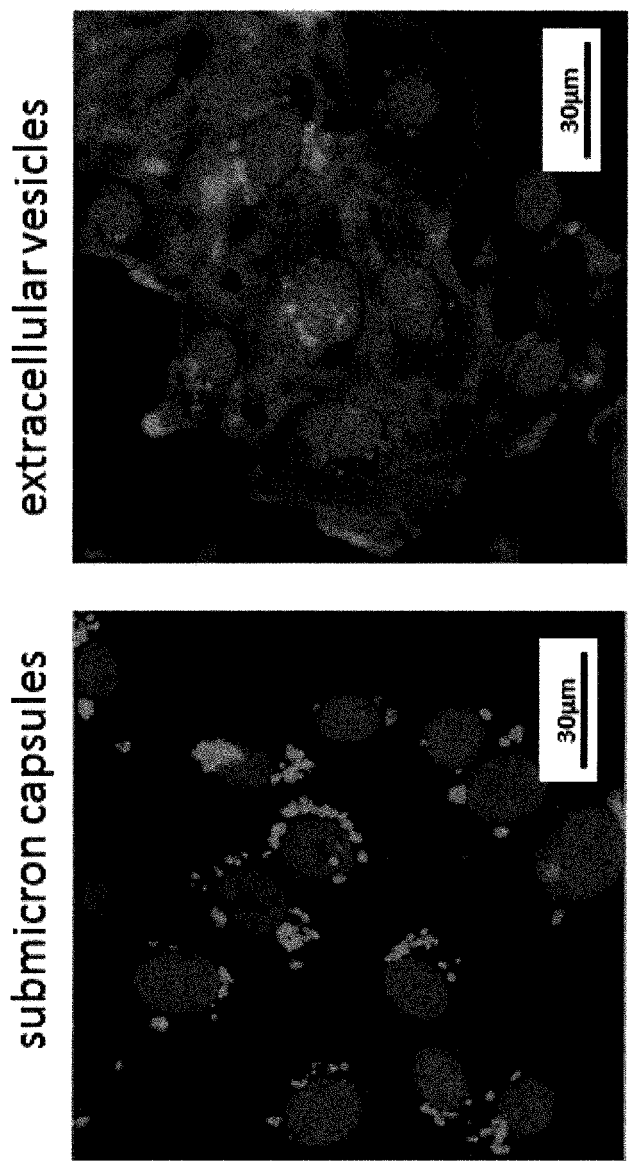
Figure 8A:
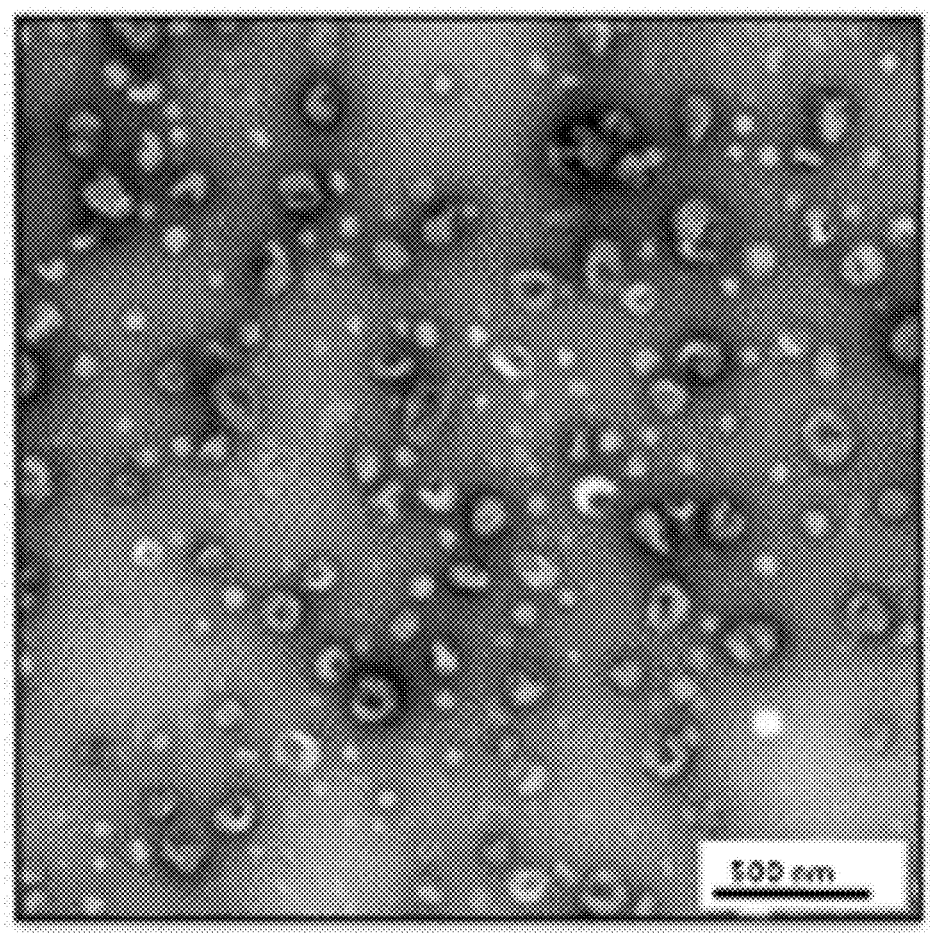
FIGS. 8A and 8B show extracellular vesicles (EV) isolated from cell culture supernatants of HT1080 cells.
Figure 8B:
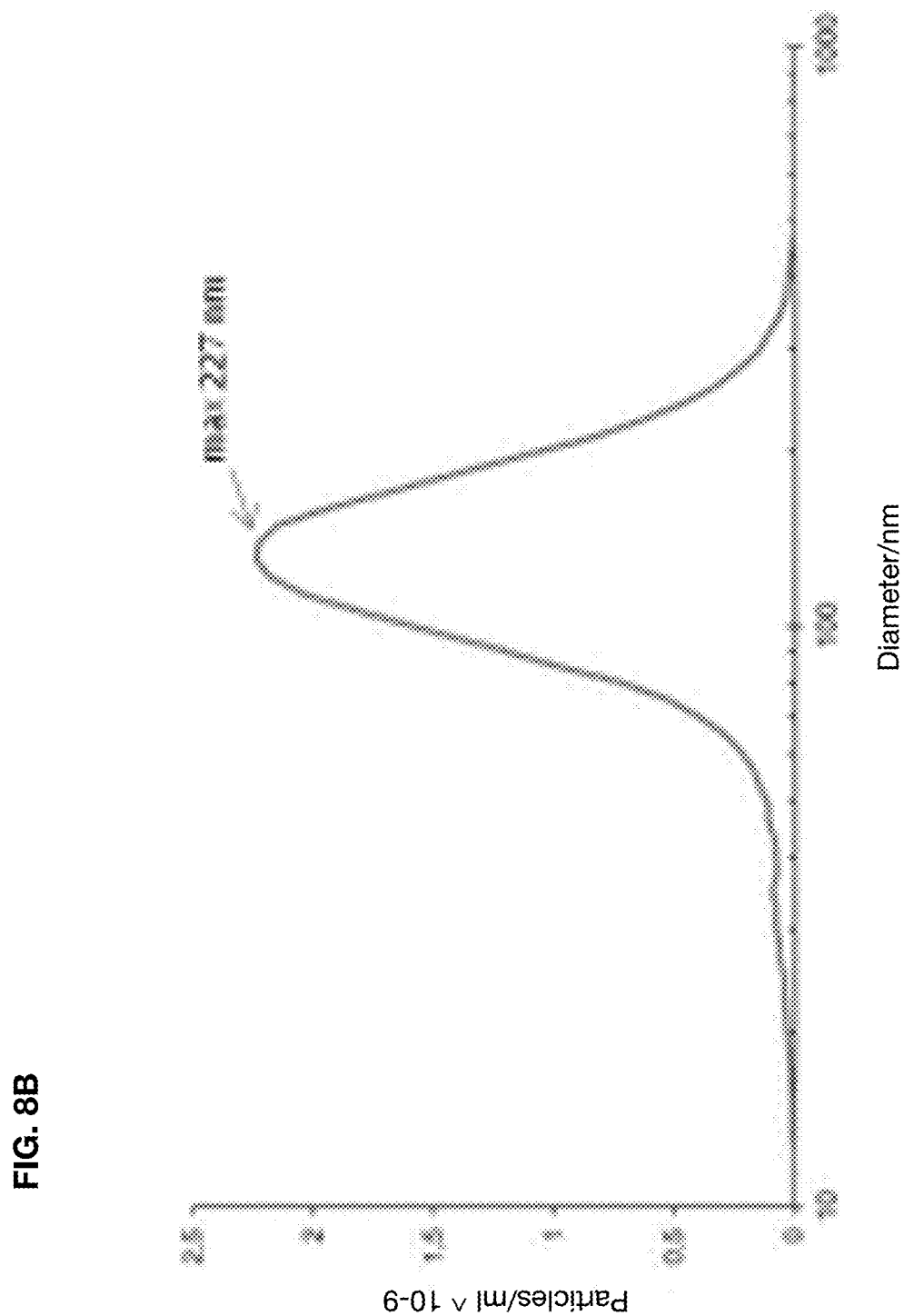

After conventional quality controls using electron microscopy and nanoparticle tracking analysis (FIGS. 8A and 8B), the vesicles were labeled with PKH26 membrane dye for their visualization within the cells. Tumor cells were treated with the vesicles and capsules for 8 h. Next, the cells were fixed and stained with DAPI and phalloidin for samples treated with vesicles. Analysis of images by confocal microscopy revealed remarkably similar intracellular localization of capsules and vesicles (FIG. 3B). Both were visualized in the perinuclear regions and endocytic compartments supporting our rationale that nanosized capsules will be delivered to the same intracellular compartments as the vesicles, possibly employing their intracellular routes. Based on current knowledge, one can speculate that in contrast to microcapsules, which have been frequently characterized in previous works and are reported as being internalized mostly by a cholesterol-, and caveolin-dependent pathway and as being located in the cytoplasm, nanocapsules, can, due their smaller size, be encapsulated via clathrin-mediated endocytosis, which is described as one of the main pathways for the internalization of exosomes. However, since not only particle size but also charge, types of recipient cell and perhaps other as yet undefined parameters play a role in determination of the internalization pathways, more efforts will be required to characterize the intracellular traffic routes of nanocapsules in different cell types.

Example 4

Analysis of the Kinetic of siRNA Release

Figure 4A:
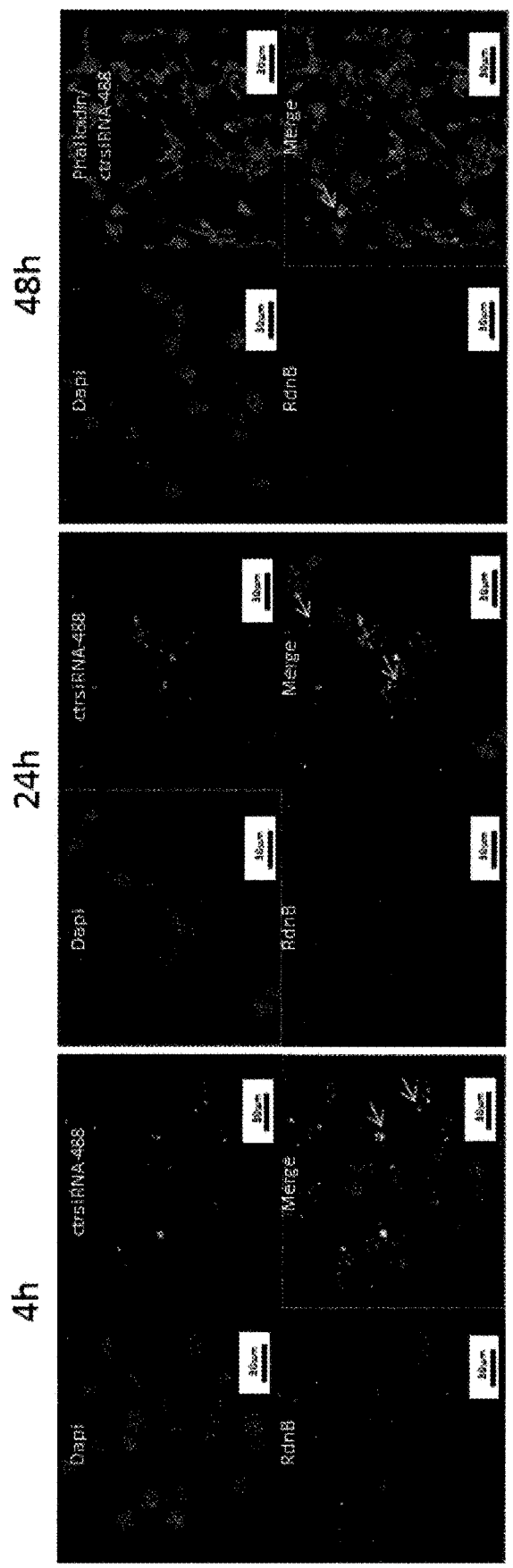
FIGS. 4A-4C show an analysis of degradation kinetic of polyelectrolyte nanocapsules.
Figure 4B:
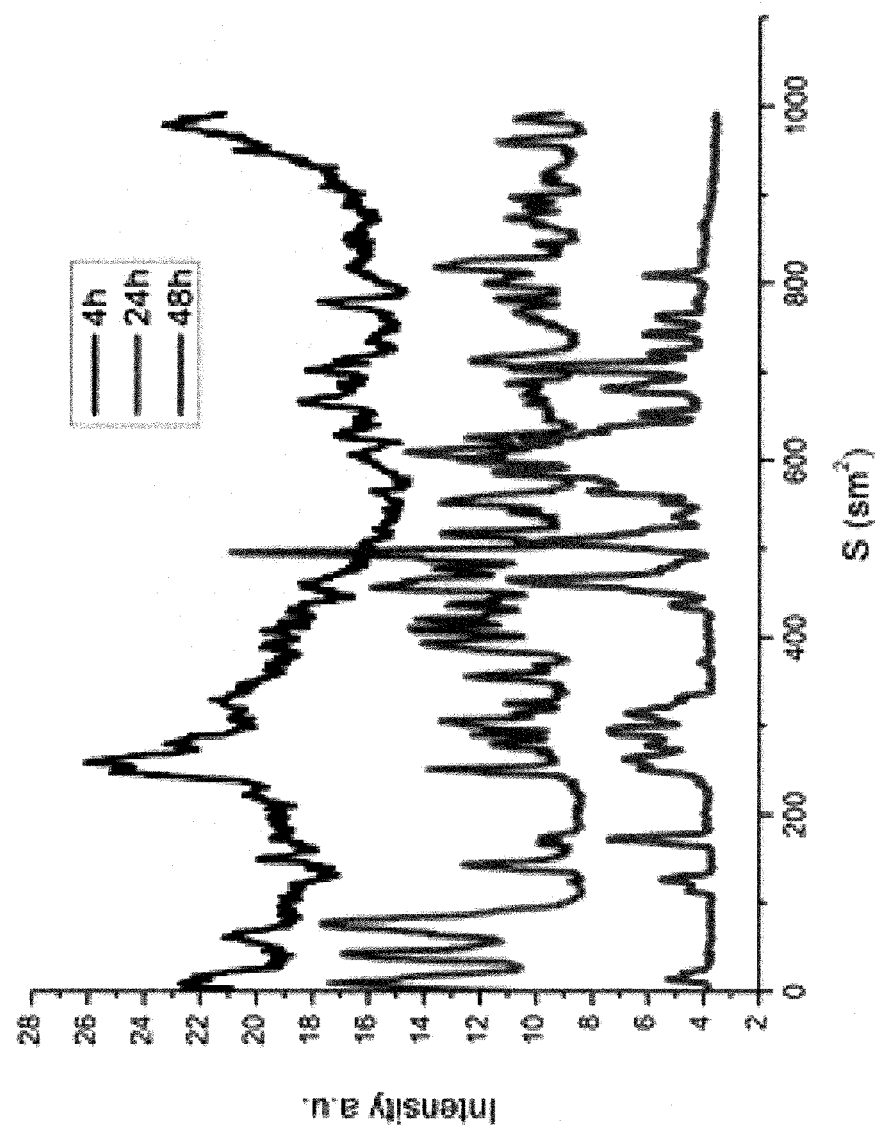
Figure 4C:
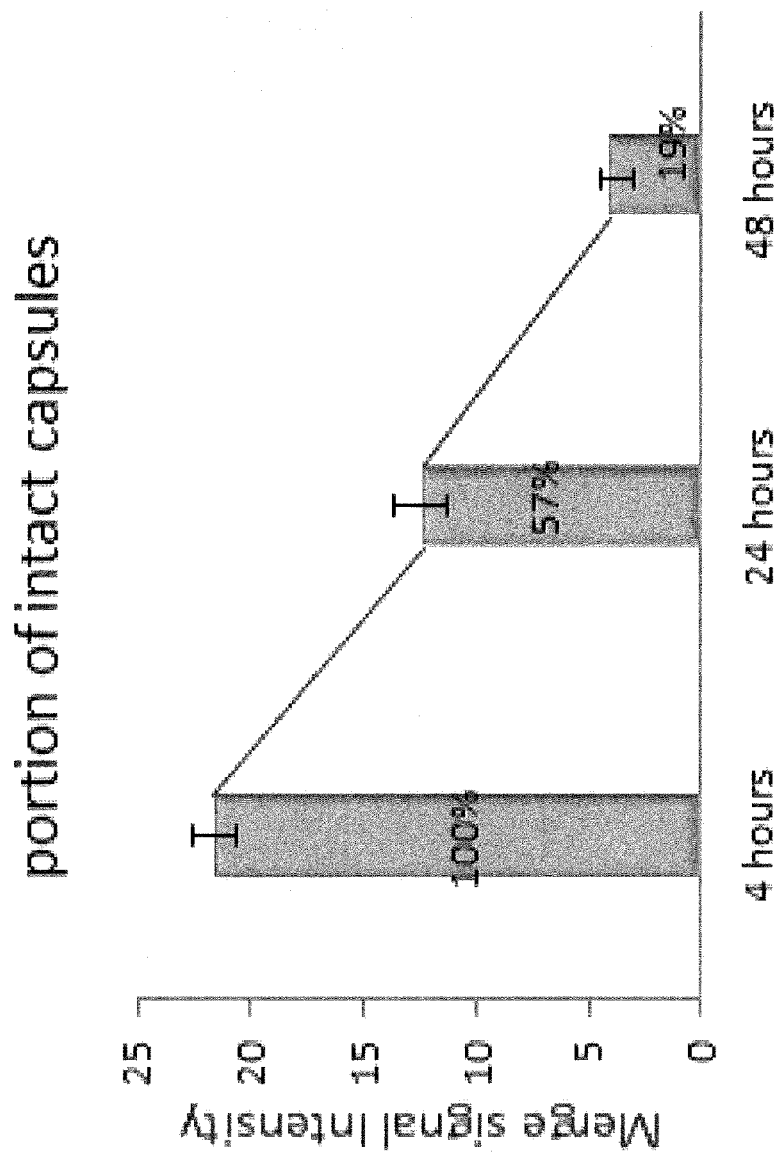

Next, kinetic of RNA release was addressed. As is shown in FIG. 4A, 4 h after treatment, the Rdn-ctrsiRNA-488 capsules were already detected within the cells. RdnB (red color) was fully merged with the siRNA-488 (green color), indicating that the capsules were intact and that the RNA was still entrapped within the capsules (FIG. 4A, left panel, arrows). The fluorescence signal was increased after 24 h, suggesting that more capsules have internalized. Only a portion of RdnB signal was merged with the siRNA-488 signal, indicating capsule degradation and release of the siRNA-488 from the capsules (FIG. 4A, middle panel, arrows).

Electron microscopy. Capsule morphologies were provided by scanning electron microscopy (SEM MIRA II LMU (TESCAN). Capsule suspension was dropped to the silicon surface, dried, coated with gold. SEM observation was carried out using an accelerating voltage of 10 kV. To visualize cells uptake and evaluate capsules, a confocal laser microscopy system was used.

Immunofluorescence. Two days before experiment, 1.5× 104 cells/well were seeded in ibidi 8-well μ-slide chamber. On the day of staining, cells were fixed with 4% paraformaldehyde for 5 min at 37° C., washed and permeabilized with 0.1% Triton-X 100. For staining, cytoskeleton phalloidin conjugated with either Alexa488 or Alexa594 fluorophores was applied for 1 h and washed. Next, the nuclei were stained with DAPI for 20 min at room temperature, washed and incubated with Prolong Diamond anti-fade mountant, allowed to heal overnight at room temperature. Images were taken using a Leica confocal microscope (Leica TCS SP2 AOBS) equipped with a HCX PL APO 63×NA 1.4 oil immersion objective. Images for the different fluorophores were scanned sequentially. Further image processing was carried out using image J software.

Image analysis. For quantitative evaluation of green signal intensity, Image J freeware was used. The experiment was done in biological triplicates. For statistical analysis, five images of each delivery method were taken. For each image, intensity distribution graph of the green signal over the area was plotted. Area statistics was calculated for the complete image and the average intensity value was calculated.

A decrease of the fluorescent signal was observed after 48 h of incubation, suggesting that majority of capsules had degraded. Only few large red spots, which could represent agglomerated dye, were detected in the cytoplasm partly colocalized with actin filaments or residual RNA, both stained in this image in green (FIG. 4A right panel, arrows). Quantitative analysis revealed that about 43% of the capsules had degraded after 24 h and about 81% after 48 h (FIG. 4B, C). This indicates that due to the intracellular proteolytic activity, the majority of the capsules had degraded between 24 and 48 h, allowing consecutive release of active RNA molecules within the cells and supporting their sustainable effect and high efficiency, which we addressed in our next experiments.

Example 5

Efficient GFP Knockdown in Cancer Cells

Figure 5A:
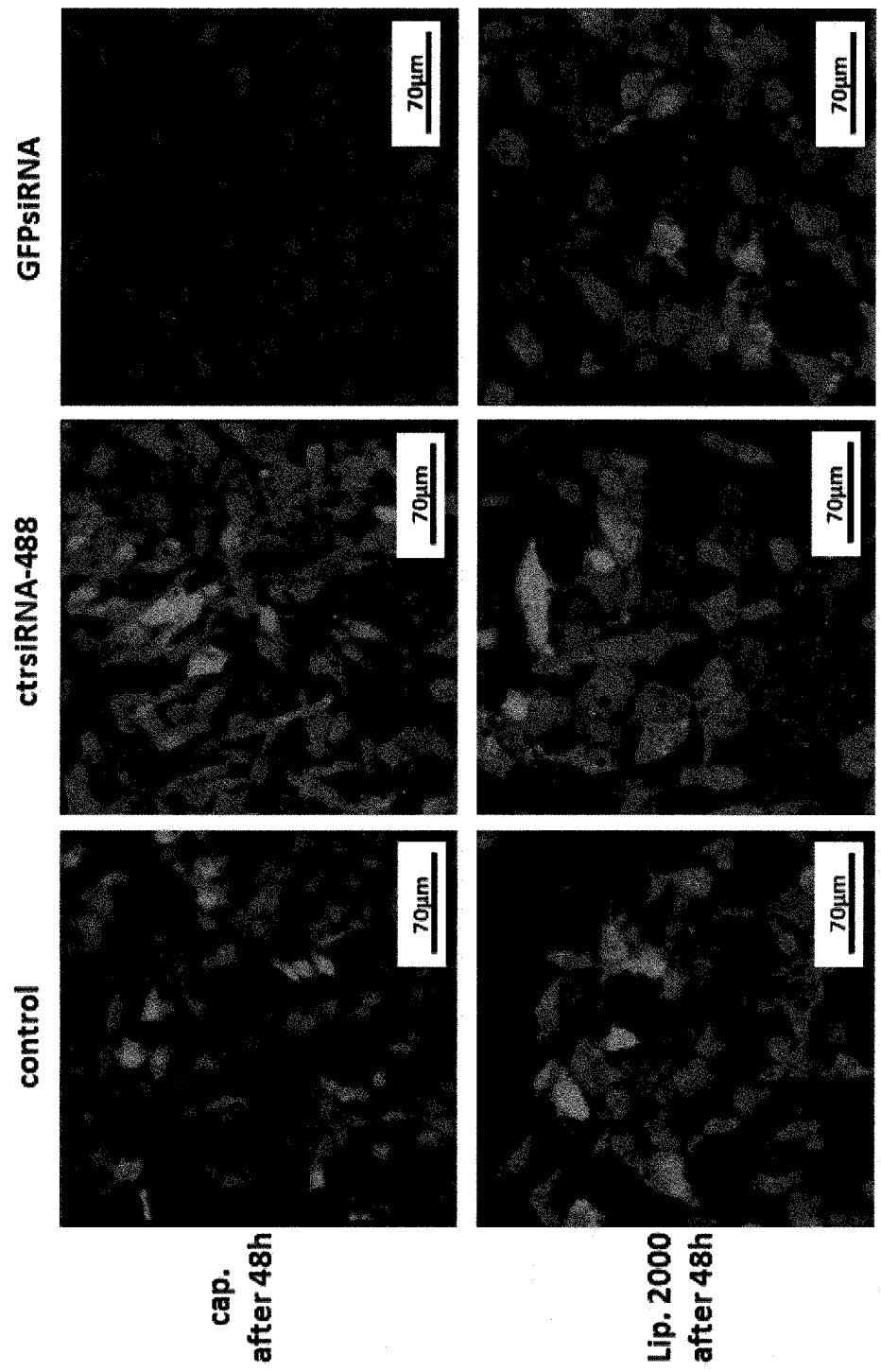
FIGS. 5A-5C show the efficient GFP knockdown by transfer of the GFPsiRNA in biodegradable nanocapsules in HT1080-GFP cells.
Figure 5B:
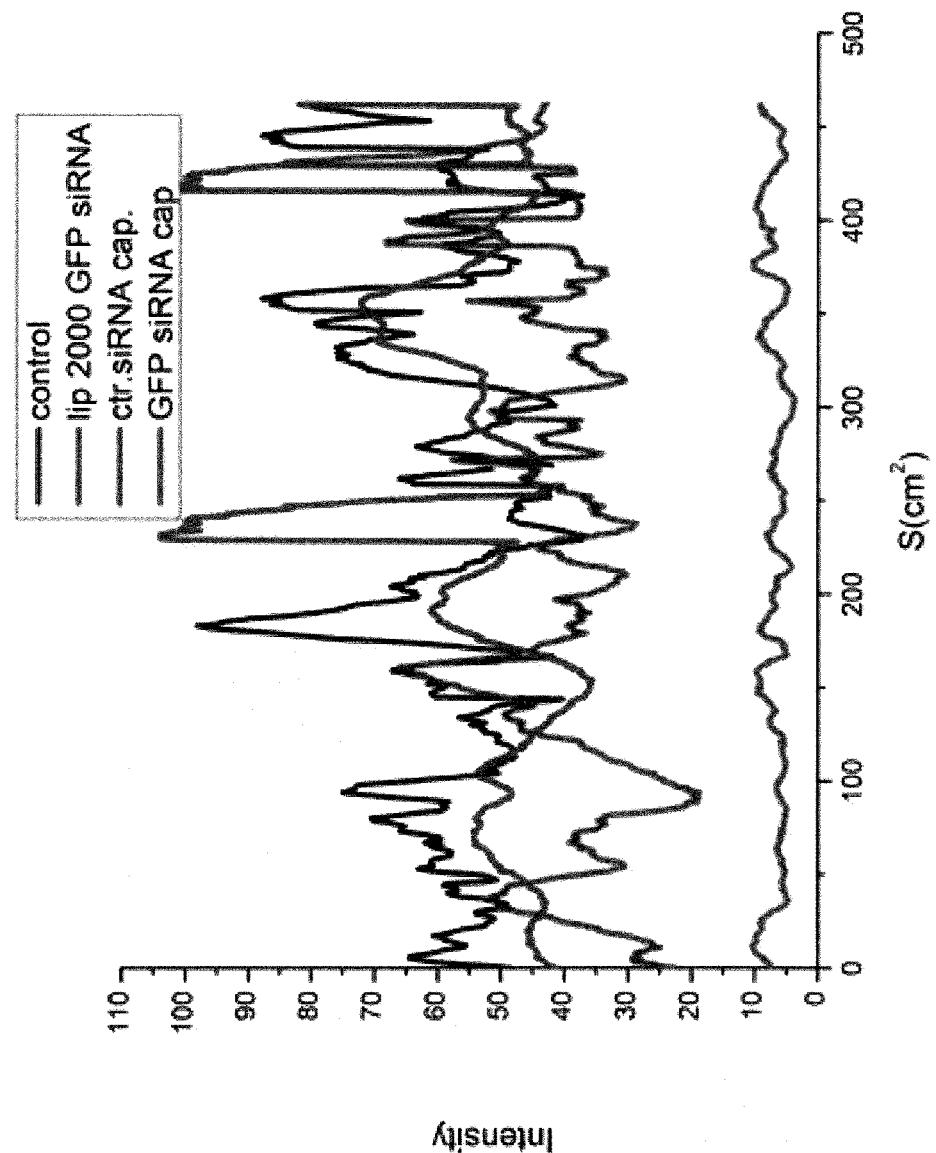
Figure 5C:
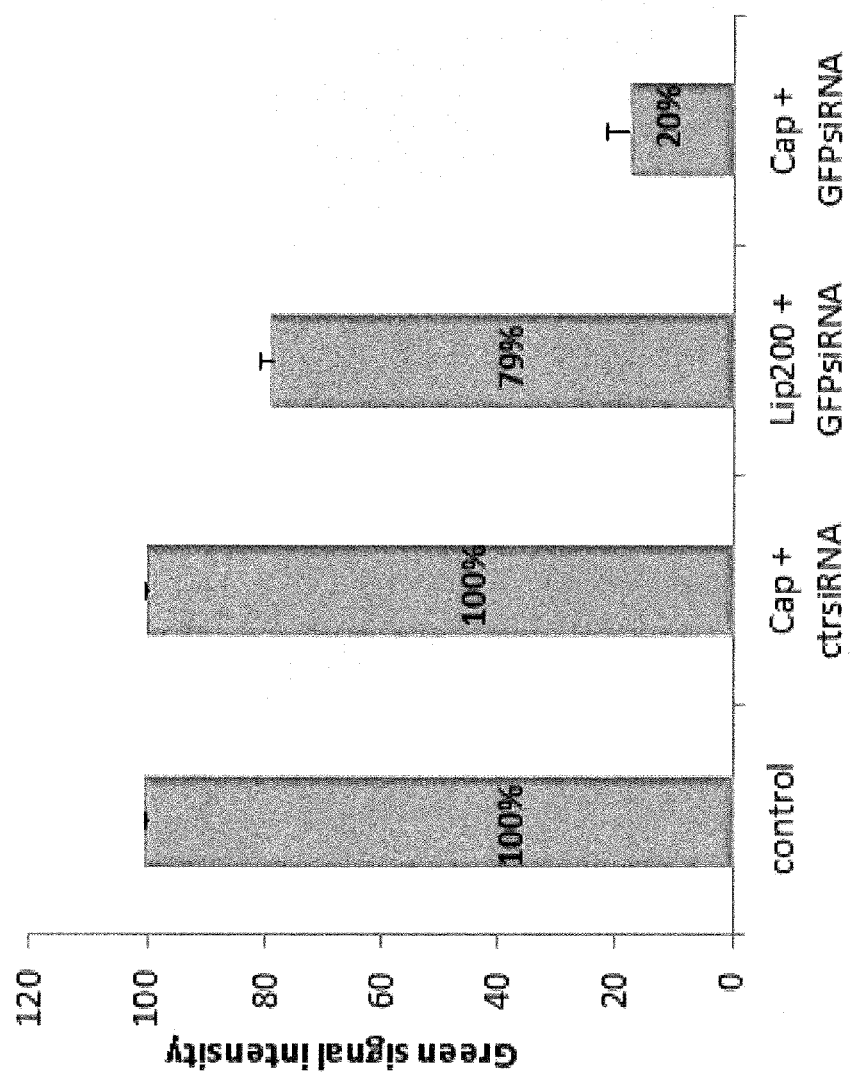
Figure 9A:
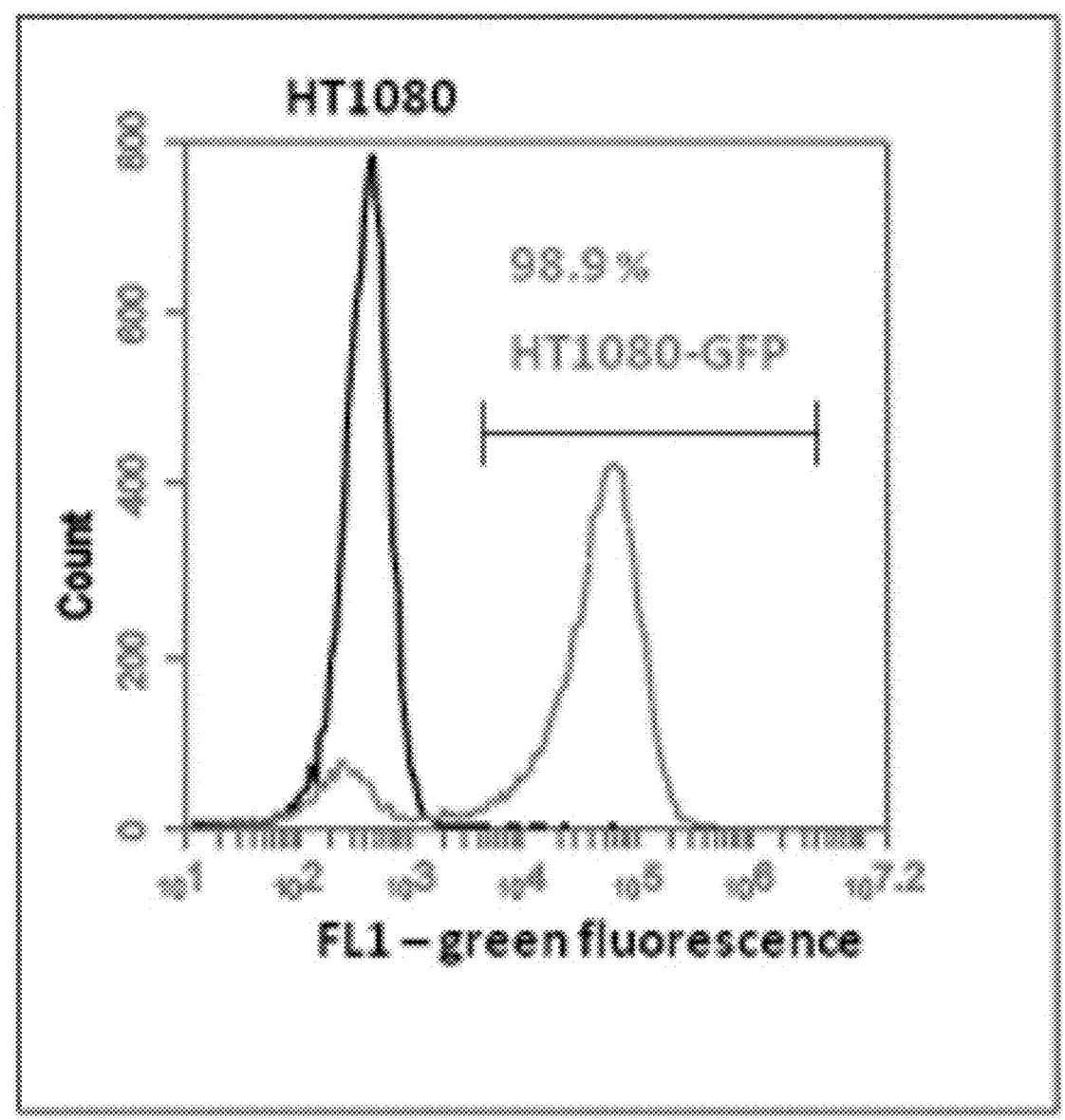
FIGS. 9A and 9B show that the HT1080 cells were stably transfected with the GFP-expressing plasmid and sorted for GFP expression.
Figure 9B:
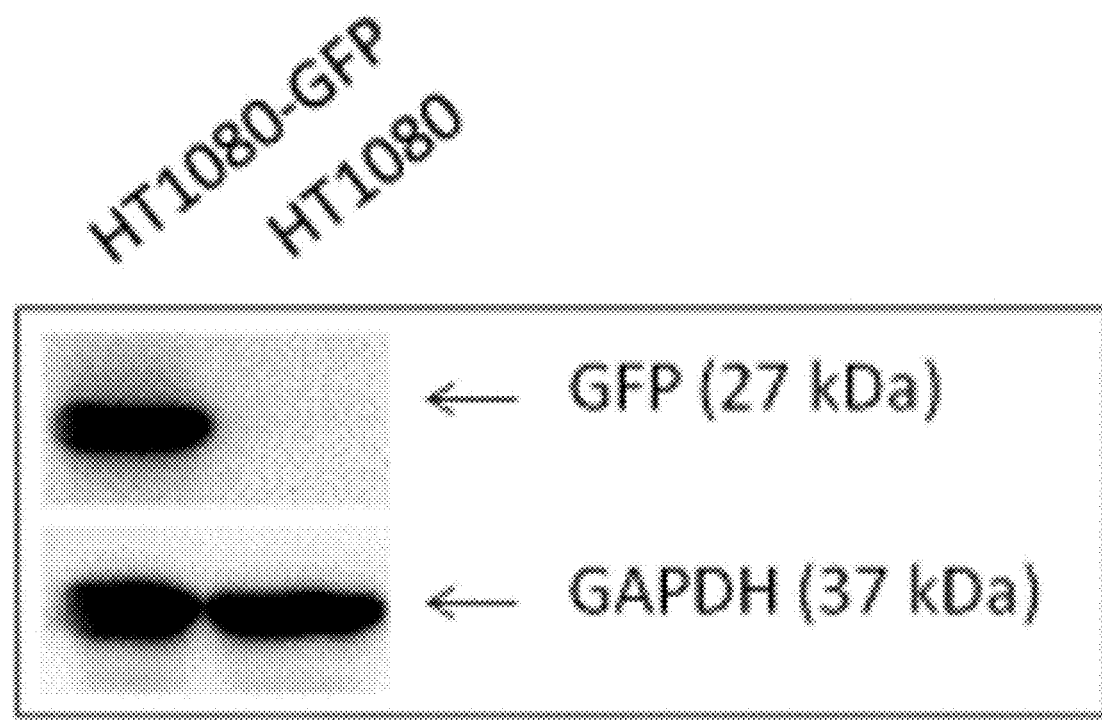
Figure 10:
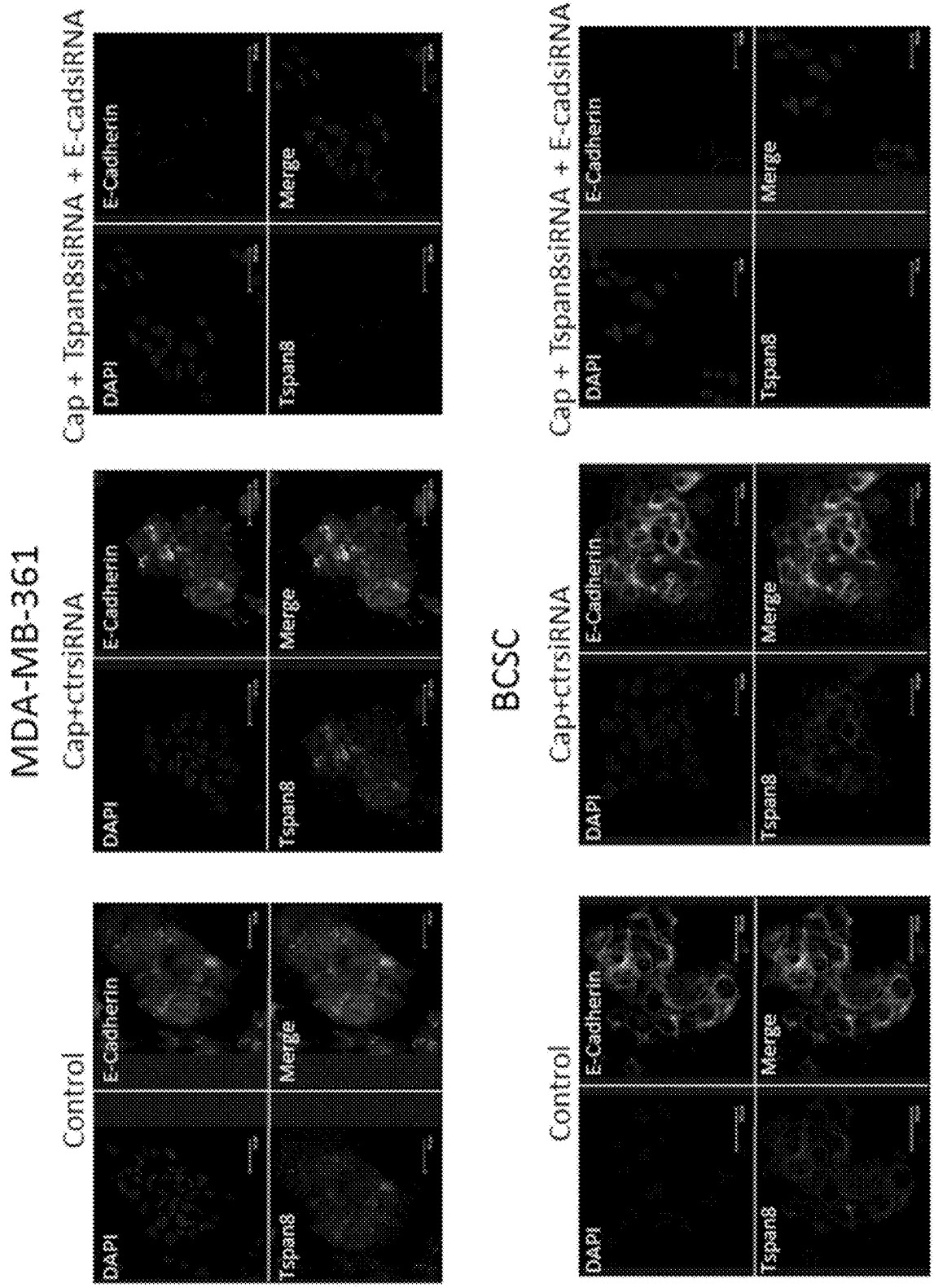
FIG. 10 shows the knockdown of Tspan8 and E-Cadherin using nanocapules loaded simultaneously with corresponding siRNAs. The MDA-MB-361 breast cancer cells and breast cancer stem cells (BCSC), which are excessively characterized were treated with capsules containing a mixture of the siRNAs targeting E-Cadherin and siRNAs targeting Tspan8, which were loaded as a mixture between the PARG layers analogous to the application of a single siRNA. As a control, untreated cells and scrambled oligonucleotides were applied. Images were taken 48 hours post treatment. Strong diminishment of the Tspan8—and E-Cadherin—specific staining was observed in both type of cells, supporting that the nanocapsules are universally applicable for both, cell lines and primary cells, e.g. breast cancer stem-like cells. These data demonstrate a way of manipulation of tumors in vivo, including cancer stem cells, also referred as cancer-initiating cells, inaccessible until now with conventional non-viral methods of gene transfer.
Figure 11:
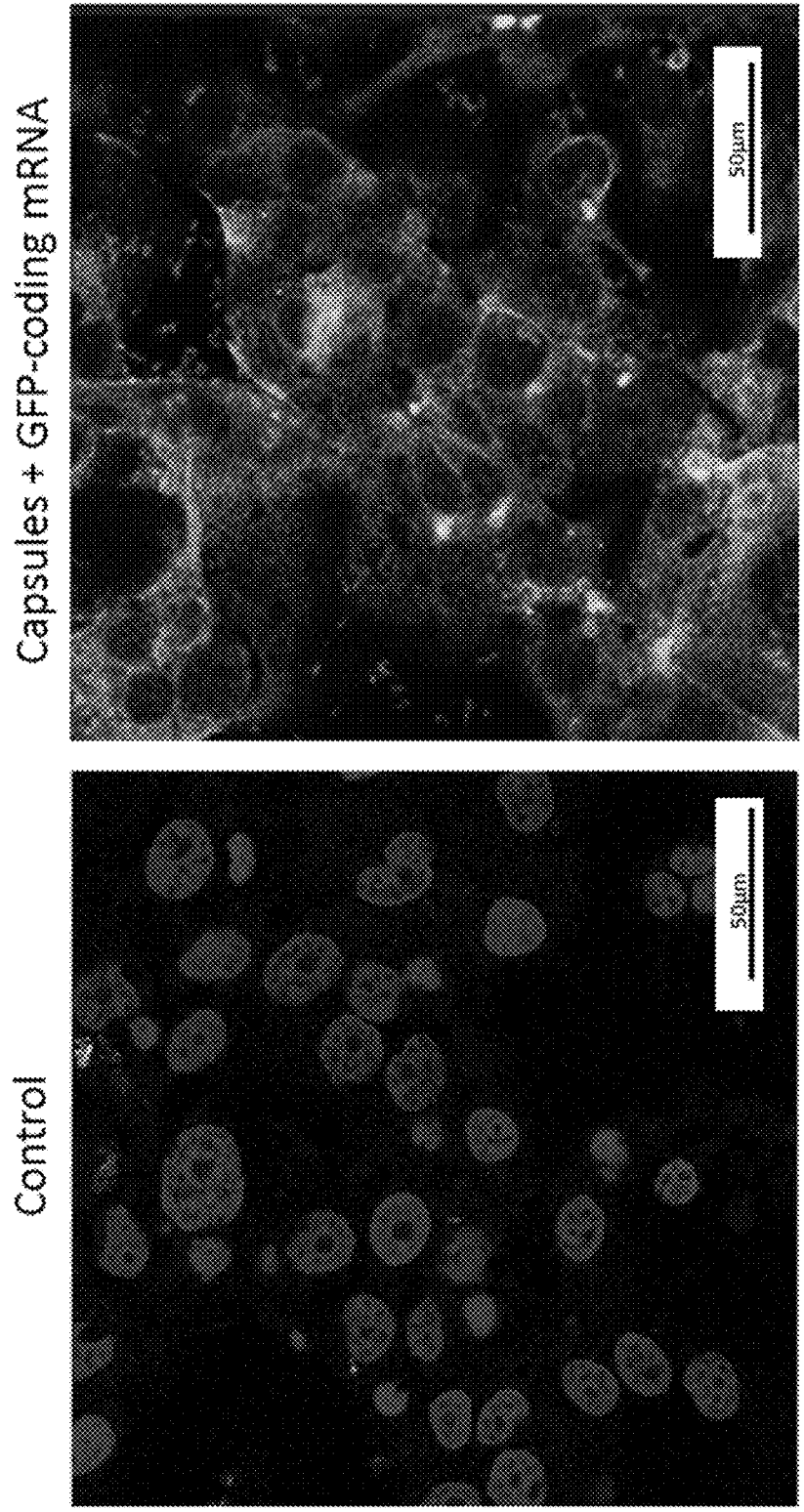
FIG. 11 demonstrates the transfer of the full length functional GFP mRNA in breast cancer stem-like cells. To test if nanocapsules can be used for transfer of functional mRNA, GFP mRNA supplemented with RNase Inhibitor was incorporated between the PARG layers. Images were taked 48 hours post-treatment. Green fluorescence was obtained in BCSC cells treated with nanocapsules, whereas the untreated cells did not exhibit green fluorescence.
Figure 12A:
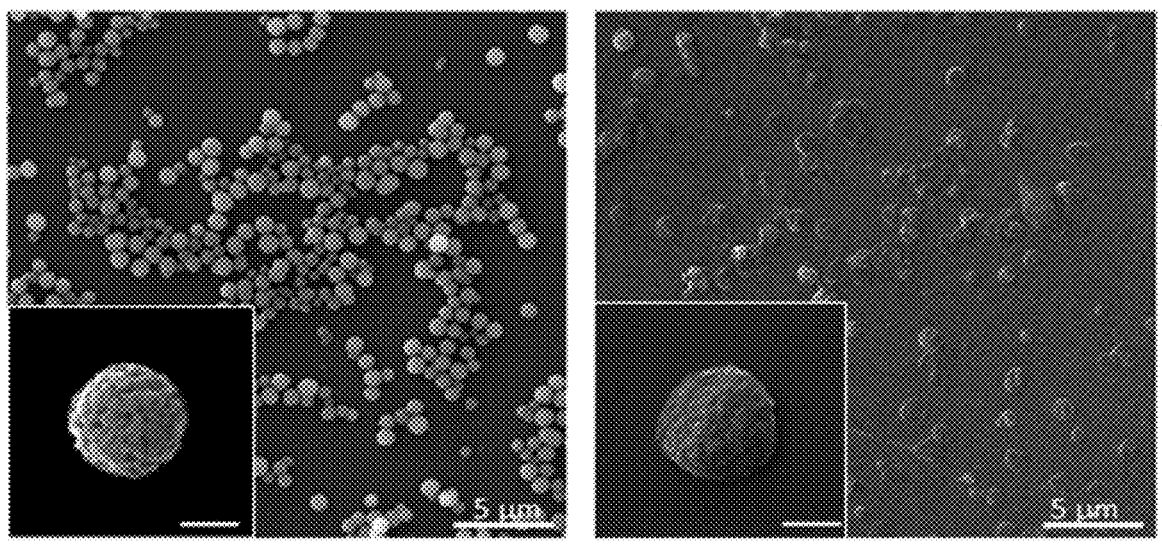
FIGS. 12A-12C show the transfer of genetic material to primary T cells and CD34+ hematopoietic progenitor cells. To adapt nanocapsules-based gene transfer for application on primary immune cells and hematopoietic progenitor cells, protocol for capsule preparation was slightly changed in order to produce capsules of a smaller size to ensure efficient uptake and low toxicity as described in Example 8.
Figure 12B:
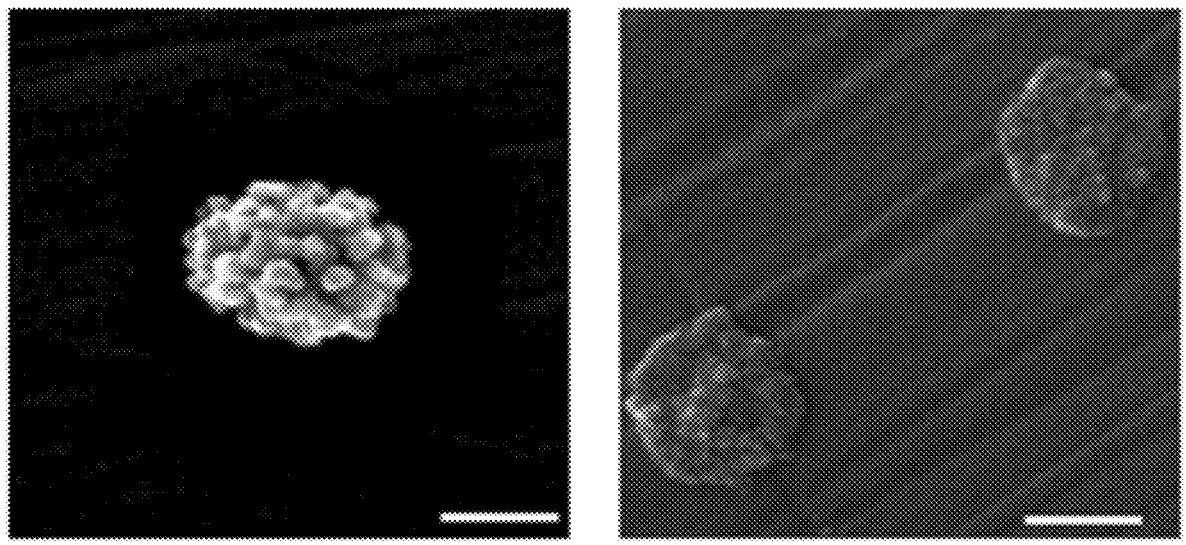
Figure 12C:
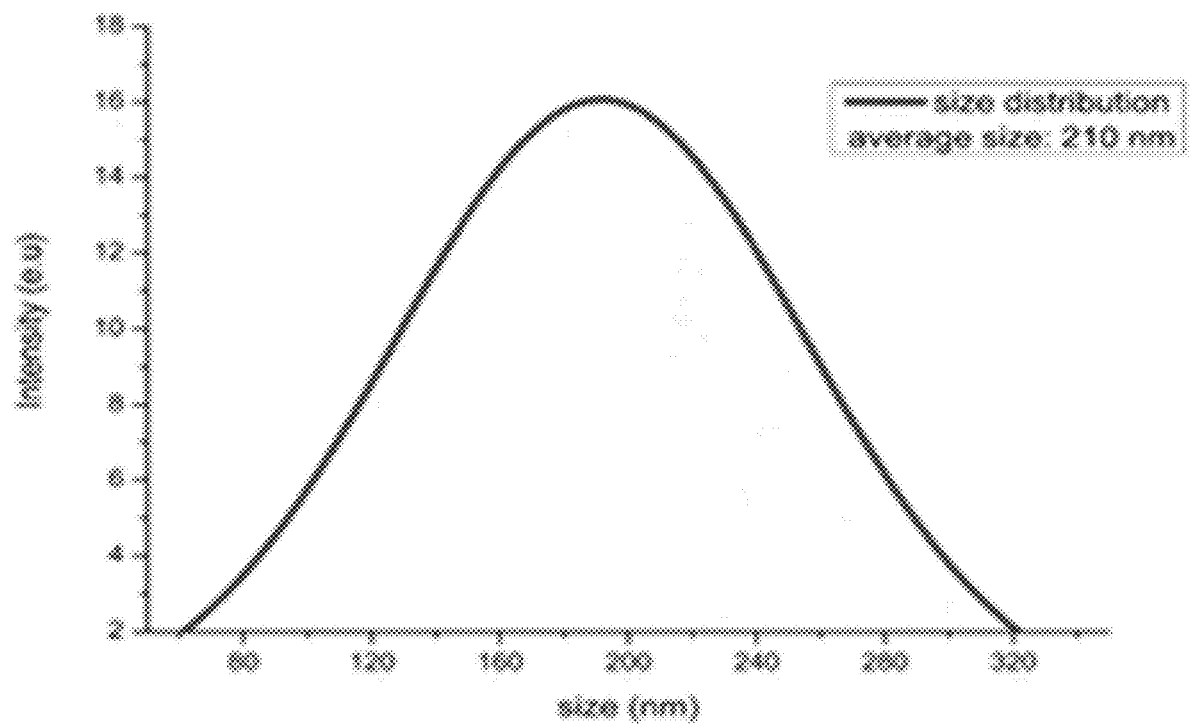
Figure 13:
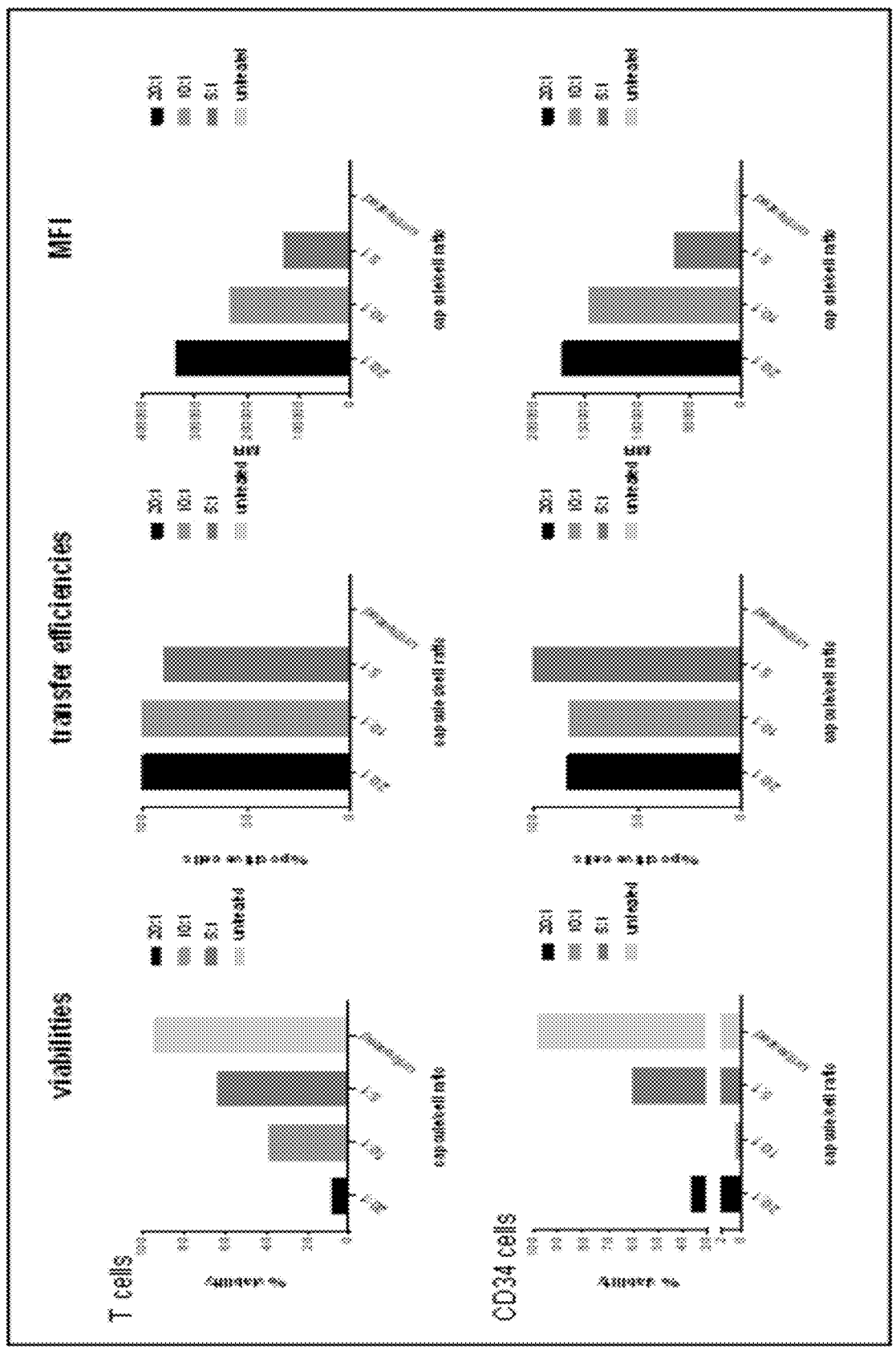
FIG. 13 shows the uptake efficiency and viability of CD34 and T cells treated with Rhodamine-labeled capsules. The details of the experiment are disclosed in Example 9.

To show the universality of our approach, conventional method of knocking down GFP was employed, stably overexpressed at a high level in HT1080 cells. This is shown in FIGS. 9A and 9B. For this purpose, capsules loaded with a control siRNA (AllStars negative control siRNA labeled with Alexa488 dye, ctrsiRNA-488), and capsules loaded with siRNA specific for GFP (GFPsiRNA) were produced; 20 capsules/cell were used for treatment of the HT1080-GFP cells (FIG. 5A upper panel). Additionally, cells were transfected with Lipofectamine 2000 using the same amount of siRNA, corresponding to $2.5 \times 10^{-4}$ pmol siRNA/cell (FIG. 5A, bottom panel). No residual GFP signal could be detected in the cells treated for 48 h with the capsules containing GFPsiRNA, in contrast to the cells transfected with GFP-siRNA using Lipofectamine 2000. Quantitative analysis based on calculation of the intensity of the green fluorescence signal (FIG. 5B) revealed 80% reduction of green fluorescence in the cells treated with nanocapsules filled with GFPsiRNA and 21% reduction of GFP signal in the cells transfected with Lipofectamine 2000; no unspecific effect was observed by the application of capsules loaded with the control siRNA (FIG. 5B, 5C).

These results suggest that biodegradable nanocapsules possess utmost high transfer efficiency of RNA molecules with no toxic effect. Interestingly, by application of comparable biodegradable microcapsules 1-3 µm in diameter considerably higher loading capacity using conventional loading technique into the $CaCO_3$ core was recently reported. However, to enrich a comparable knockdown efficiency of 80%, 500 pmol/10 capsules/cell siRNA were required as described previously, which is $2 \times 10^6$ fold more than used in the current work applying $2.5 \times 10^{-4}$ pmol siRNA/20 capsules/cell. This comparison argues strongly that microcapsules definitely possess a higher loading capacity and may be favorable for delivery of substances to target cells if a high amount of a payload is the primary goal. However, for transfer of small amounts of regulatory molecules such as RNA or DNA, application of biodegradable nanocapsules allowing highly efficient transfer of payloads to target cells may be favorable.

Example 6

Figure 6A:
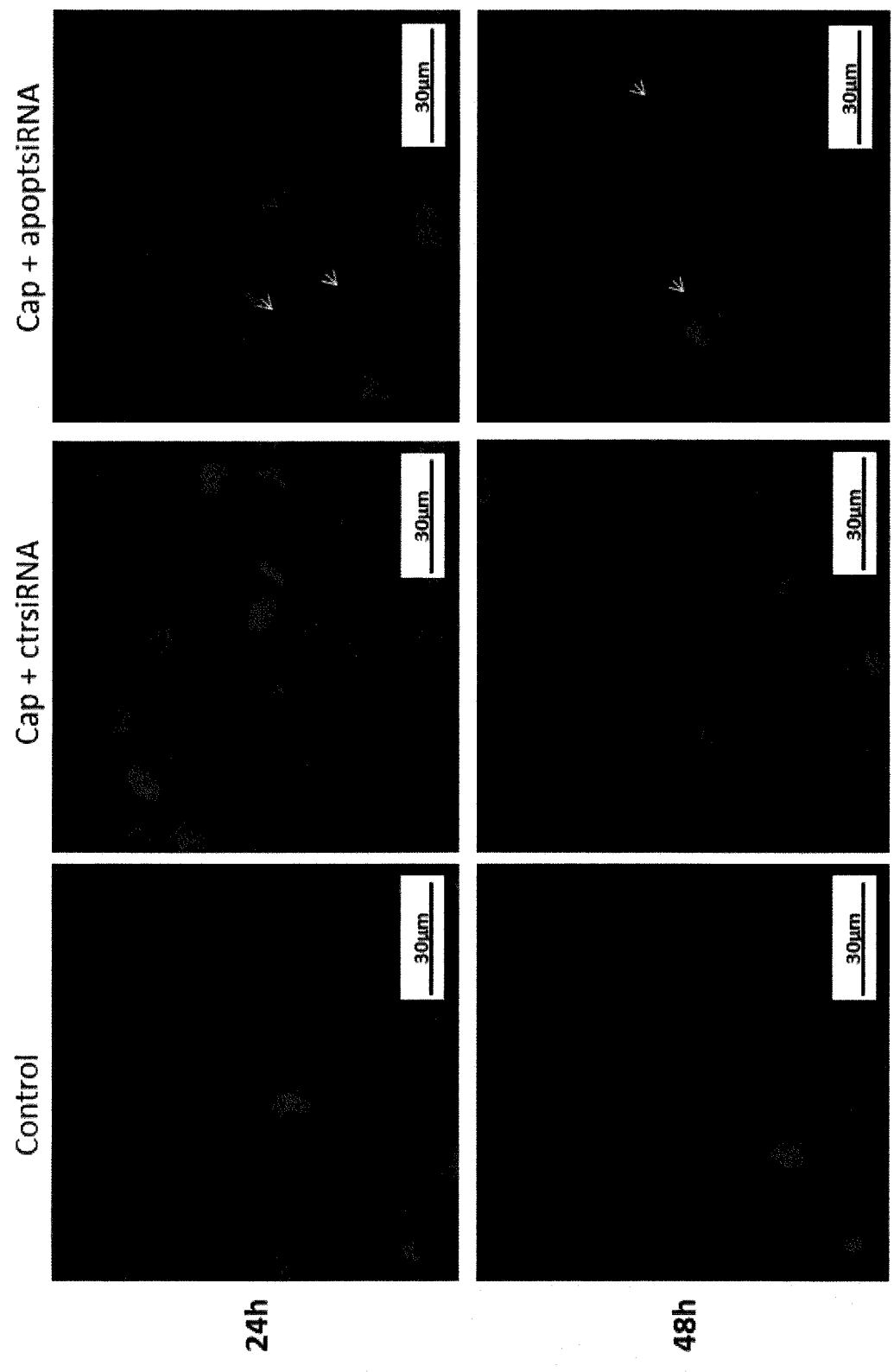
FIGS. 6A and 6B show an efficient apoptosis induction by transfer of AllStar Cell Death siRNA in biodegradable nanocapsules in HT1080 cells.

High Efficiency of Capsule—Mediated Cancer Cell Death by Transfer of Pro-Apoptotic siRNAs Increased resistance to apoptosis, enabling survival under abnormal growth stimulation and various forms of cellular stress, such as DNA damage, hypoxia, or nutrient deprivation are among the hallmarks of cancer cells. Consequently, strategies for a specific targeting of cancer cells and apoptosis induction may provide a rational basis for development of new therapeutic tools, for example, by transfer of apoptosis-inducing agents into tumor cells. Therefore, we tested whether transfer of corresponding siRNAs by capsules may be sufficient to induce apoptosis in cancer cells. For this purpose, capsules were loaded with AllStars Cell Death Control siRNA (Qiagen) containing highly potent validated siRNAs targeting ubiquitous cell survival genes. To allow quantification of transfer efficiency and functionality, cell phenotype was controlled after 24 and 48 h of incubation with capsules by staining of the cells with a tubulin-specific antibody for cytoskeleton and DAPI for nuclei. As it is shown on the FIG. 6A, after 24 h of treatment both viable cells and fragmented nuclei characteristic for apoptosis could be detected (FIG. 6A, upper panel, white arrows), whereas only few cells with fragmented nuclei characteristic for apoptosis could be detected after 48 h (FIG. 6A, bottom panel, white arrows). This result shows that transfer of siRNA by capsules is sufficient to induce apoptosis in cancer cells and is consistent with the observation of capsules degradation. This shows that the majority of the capsules degrade between 24 and 48 h, suggesting an enhancement of siRNA effect within this time frame.

Figure 6B:
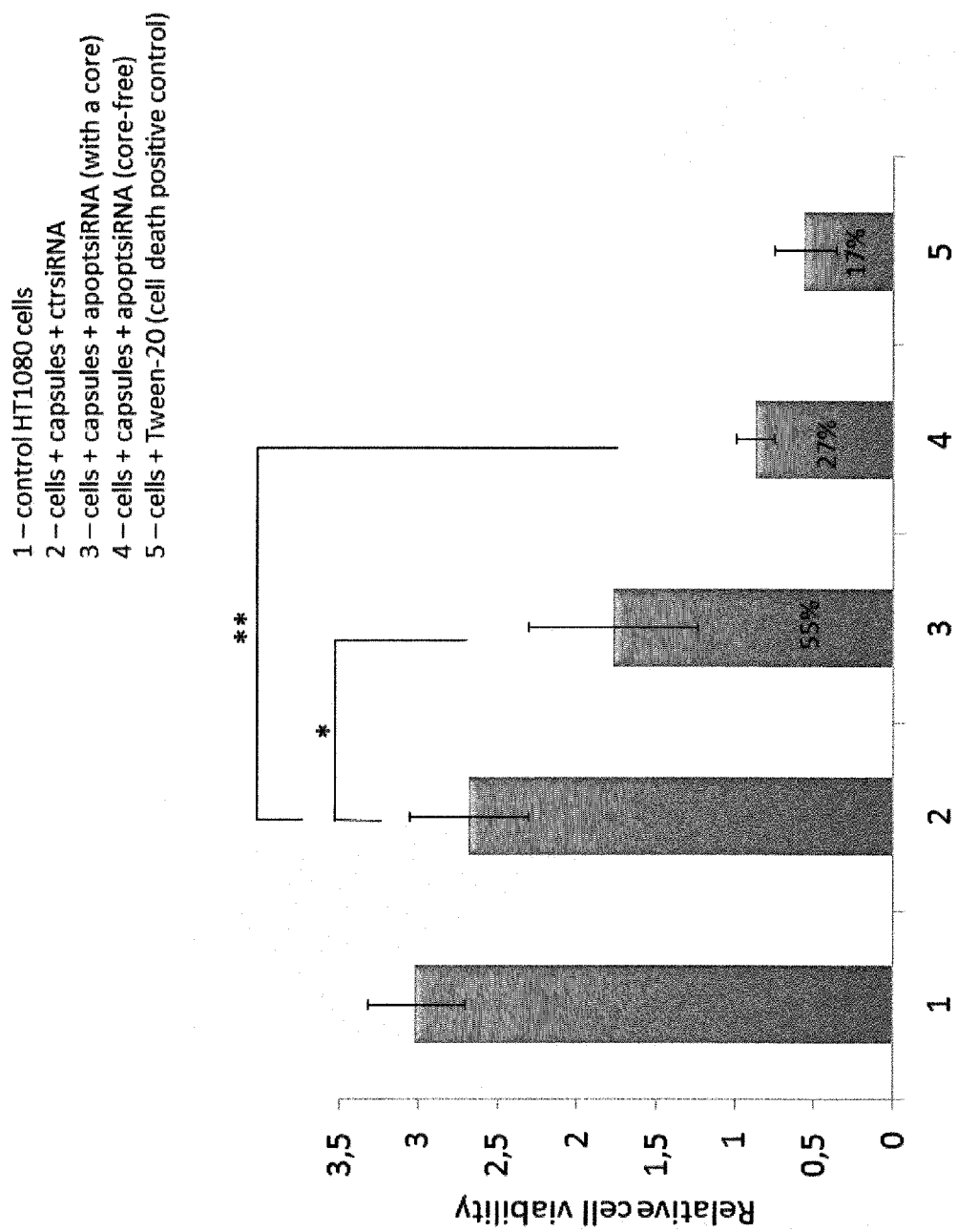

A quantitative analysis using a WST-1 viability assay was performed. Additionally, efficiency of capsules still containing a $CaCO_3$ core and core-free capsules was compared (FIG. 6B). The data demonstrate that treatment of cells with capsules containing a control siRNA exhibited no significant impact on cell viability. Application of capsules with a core led to 45% reduction of cells viability, whereas application of core-free capsules loaded with apoptotic siRNA resulted in 73% reduction of cell viability, which is comparable with the effect of Tween-20 detergent, disrupting cell membranes and used standard wise as a positive control for cell death, and showing 83% efficiency if measured by WST1 assay (FIG. 6B). These results further support efficiency and usability of biodegradable core-free nanocapsules for transfer of functional RNA molecules. By application in a ratio of 20 capsules/cells corresponding to $2.5 \times 10^{-4}$ pmol siRNA/cell, 80% functional efficiency can be reached, as demonstrated by GFP knockdown and apoptosis induction, showing no unspecific or toxic effects, which, based on the current state of technology, is one of the most efficient tools for targeted delivery of regulatory RNA.

Example 7

Figure 7A:
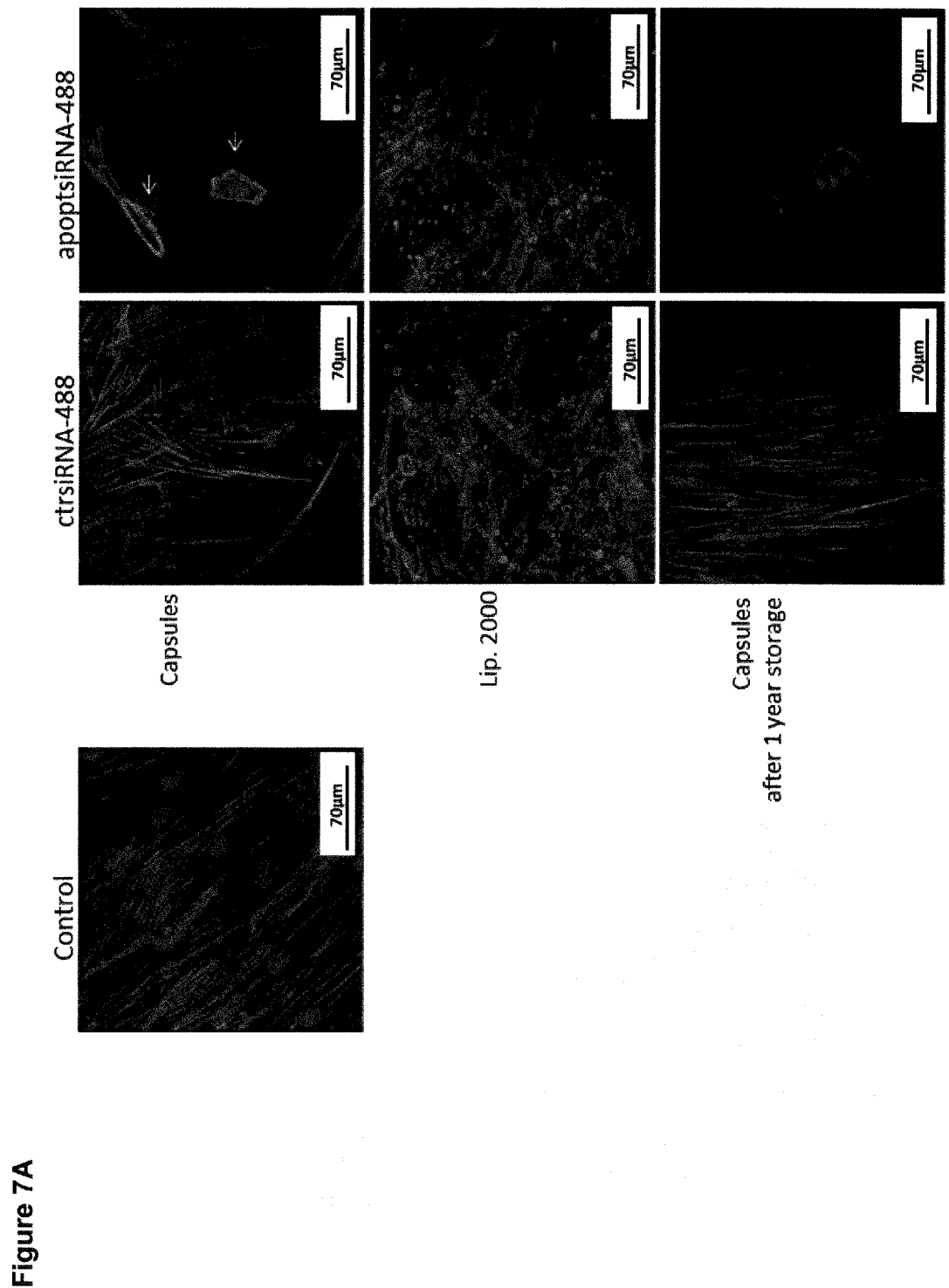
FIGS. 7A and 7B show an application of nanocapsules for transfer of the pro-apoptotic AllStar Death Control siRNA in mesenchymal stem cell (MSCs).
Figure 7B:
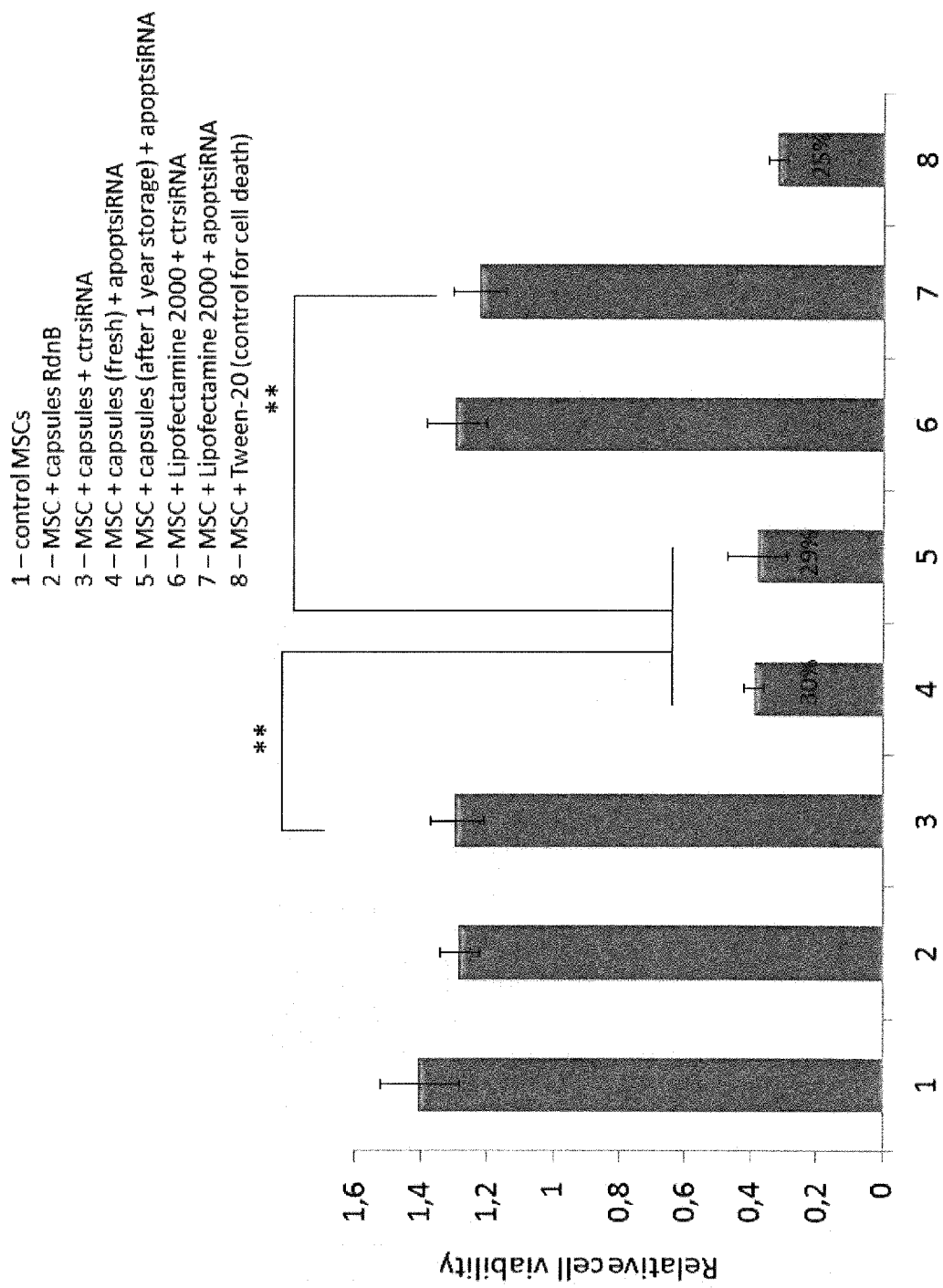

Efficient Apoptosis Induction by Transfer of Pro-Apoptotic siRNA to the Mesenchymal Stem Cells and Stability Test of siRNA in the Capsules The delivery system of the present invention was tested for RNA delivery to mesenchymal stem cells (MSCs) due to the therapeutic applications envisaged for these cells. Consequently, development of an efficient, easily accessible technique allowing MCSs manipulation that is compatible with GMP (good manufacturing practice) is exceptionally relevant. Therefore, polyelectrolyte nanocapsules were tested for RNA delivery into MSCs using AllStars Cell Death Control and AllStars negative control siRNAs as described above. Forty eight hours after treatment, MSCs were stained with phalloidin and DAPI for visualization of treatment effect using confocal microscopy. Application of apoptosis-inducing siRNA resulted in a strong reduction of cell number; remaining cells exhibited reduction of cytoplasma volume and nuclei fragmentation (FIG. 7A, upper panel, white arrows). Additionally, conventional transfection of siRNA using Lipofectamine 2000 with equal amount of siRNA/cells was performed as a control. A considerable change in cell number was not observed (FIG. 7A, middle panel).

Because stability counts as one of the important parameters for choice of delivery method, functionality of capsules stored for 1 year at +4° C. was additionally tested. As is shown in FIG. 7A, MSCs treated with the capsules and stored for 1 year, exhibited similar phenotype as MSCs, treated with freshly prepared capsules (FIG. 7A, bottom and upper panels, respectively). Quantitative analysis of cell viability revealed non toxicity of capsules loaded with a control siRNA, and over 80% reduction of MSC viability through treatment with capsules loaded with AllStars Cell Death Control siRNA. Both were freshly prepared after 1 year of storage, which indicates that along with such advantages as cost-, and functional efficiency, the capsules offer excellent payload stability and stable exploitation.

Example 8

Capsules Preparations for Transfer of RNA in Primary Cells $CaCO_3$ nanoparticles were prepared as described with some modification. Firstly, gelatin (3 g) was dissolved in $ddH_2O$ (50 ml) and heated to 90° C. After that, gelatin solution was rapidly mixed upon magnetic stirring with 99% Glycerol (50 ml). Taking into account that the size of valerit crystals is strictly dependent on salt concentration, 0.1M $Na_2CO_3$ (10 ml) and 0.1M $CaCl_2$ (10 ml) were mixed and stirred for 24 h. The fabricated particles were sedimented by ultracentrifugation at 40 000×g and washed with hot water (70° C.). Coating of particles with layers with and without RNA was undertaken as described previously.

Example 9

Transfer of PBMCs with Nanocapsules Comprising gRNA and Cas Protein

Peripheral blood mononuclear cells (PBMCs) were isolated using phase separation and then frozen in liquid nitrogen until used. PBMCs were thawed 4 days prior to use and let to recover for 24 hours to deplete the monocytes in RPMI complete medium [RPMI 1640 medium supplemented with 10% fetal calf serum, penicillin (100 U/ml), streptomycin (100 mg/L) and HEPES (10 mM). Then, T cells or CD34+ cells were harvested from the supernatant; T-cells were activated using anti-CD2/CD3/CD2 antibodies and cultured with RPMI complete medium supplemented with 100 U/ml of IL-2, 25 U/ml of IL-7 and 50 U/ml of IL-15 for 3 days before treatment. At day 3, $1×10^6$ activated T cells and CD34+ cells were treated with nanocapsules loaded with Rhodamine, in order to define concentration of capsules allowing maximal uptake by minimal toxicity. For T cells 10 capsules/cells and for CD34 cells 5 capsules/cells were considered as an optimal concentration.

To test applicability of nanocapsules to manipulate primary T cells, the cells were isolated as described above; the nanocapsules were loaded with Cas9 mRNA and a guide RNA (gRNA) targeting the "HEK site 4" genomic locus (PMID: 25513782). As a positive control, $1×10^6$ activated T cells were nucleofected with 5 μg of mRNA encoding Cas9 and 75 pmol of gRNA targeting the "HEK site 4" locus using the 4D nucleofector according to the manufacturer recommendation (P3 kit, EO-115 program). After transfer of capsules or nucleofection, respectively, T cells were recovered in 96-well plates for 4 days before assessing the nuclease cleavage activity at the target locus.

Figure 14:
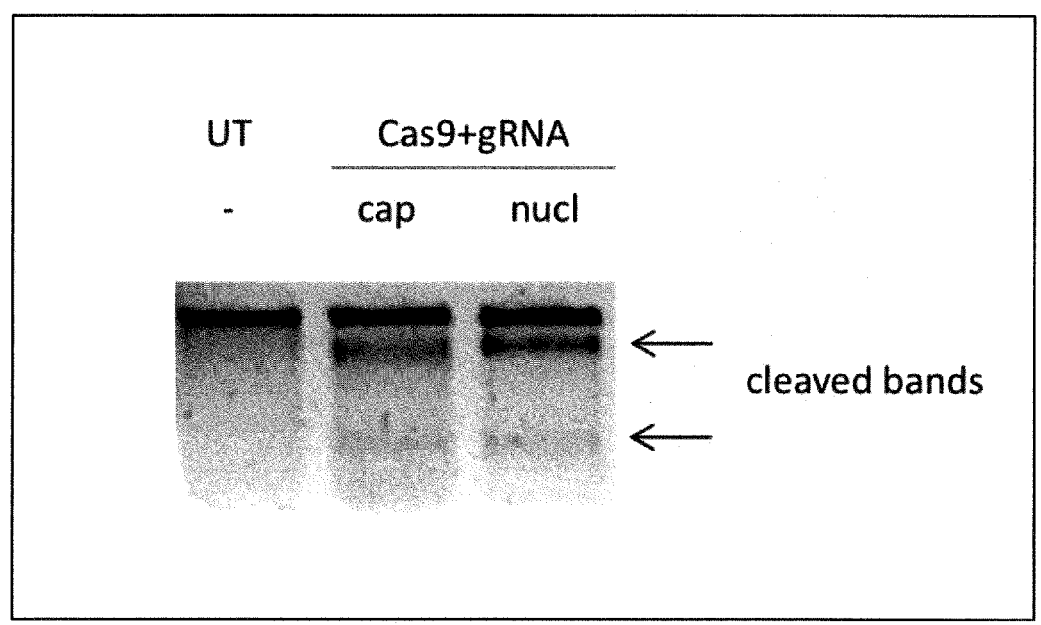
FIG. 14 shows the activity of CRISPR/Cas9 nuclease upon capsule-mediated delivery in primary T cells assessed by T7E1 assay at the "HEK site 4" locus. Cells were either left untreated (UT), or treated with capsules (cap) containing Cas9 mRNA+gRNA, or nucleofected (nuc) with 5 μg of mRNA encoding Cas9 and 75 pmol gRNA.

The activity of the nuclease was assessed by measuring the extent of non-homologous end joining (NHEJ)-mediated mutagenic repair at the target site using the mismatch-sensitive T7 endonuclease 1 (T7E1) assay. At day 4 post-transfection, cells were harvested and genomic DNA was extracted using direct lysis buffer mixed with proteinase K (20 mg/ml). An amplicon encompassing the nuclease target site in the "HEK site 4" locus was generated by PCR using the primer pair (5'-AGGCAGAGAGGGGTTAAGGT-3' (SEQ ID NO:1) and 5'-GGGTCAGACGTCCAAAACCA-3') (SEQ ID NO:2). Afterwards, amplicons were purified using QIAquick PCR Purification Kit and subjected to digestion with T7E1 as previously described (PMID: 21813459). Cleaved fragments are an indication for the activity of the nuclease at the intended target site compared to the un-transfected (UT) sample were no cleaved fragments can be observed. As shown in FIG. 14, distinct bands can be detected in the sample treated with capsules (cap) containing the CRISPR/Cas9 RNAs, thus proving evidence for efficient capsule-mediated RNA delivery into primary T cells. A similar pattern can also be detected in the positive control samples, where cells were subjected to nucleofection (nuc).

What is claimed:

1. A biodegradable multilayer nanocapsule for the delivery of at least one biologically active agent into at least one target cell, wherein said nanocapsule is core-free and characterized by at least first and second layers of biodegradable polymer laid one onto the other, whereby said at least one biologically active agent is layered onto said first layer and covered with said second layer, further wherein:
   i. said at least one biologically active agent is a nucleic acid,
   ii. said nanocapsule has a diameter of 60 nm to 150 nm, and
   iii. said biodegradable polymer forming said first layer is different from said biodegradable polymer forming said second layer.

2. The biodegradable multilayer nanocapsule according to claim 1, wherein said core-free nanocapsule comprises a void center.

3. The biodegradable multilayer nanocapsule according to claim 2, wherein said void center is free of active agent.

4. The biodegradable multilayer nanocapsule according to claim 1, characterized in that the biodegradable polymer of said first layer is dextran sulfate sodium salt and the biodegradable polymer of said second layer is poly-L-arginine-hydrochloride.

5. The biodegradable multilayer nanocapsule according to claim 1, characterized in that said nucleic acid is an RNA molecule selected from among the group consisting of: a non coding RNA, a small non coding RNA, an miRNA, an mRNA, a long non coding RNA, a synthetic analogue of RNA, a hybrid RNA/DNA molecule, an mRNA, an siRNA, a gRNA, and combinations thereof.

6. The biodegradable multilayer nanocapsule according to claim 1, characterized in that the nucleic acid is selected from among the group consisting of: DNA, synthetic DNA analogues, and hybrid DNA/RNA molecules comprising linear fragments of DNA, circle DNA, plasmids, single- and double stranded DNA, RNA/DNA hybrids and synthetic nucleic acids that are able to bind intracellular DNA or RNA fragments.

7. The biodegradable multilayer nanocapsule according to claim 1, characterized in that said at least one biologically active agent comprises a nucleic acid in combination with a corresponding protein.

8. The biodegradable multilayer nanocapsule according to claim 7, wherein said at least one biologically active agent is an RNP complex of a Cas9 protein and a suitable gRNA.

9. A biodegradable multilayer nanocapsule for the delivery of at least one biologically active agent into at least one target cell, wherein said nanocapsule is prepared by:

a. providing a core consisting of $CaCO_3$;
b. coating said core with a first layer of a first biodegradable polymer;
c. depositing onto said first layer at least one biologically active agent;
d. providing a second layer of a second biodegradable polymer over said at least one biologically active agent, wherein said second biodegradable polymer is different from said first biodegradable polymer used in forming said first layer in step b);
e. dissolving said core so as to yield a core-free biodegradable multilayer nanocapsule;
further wherein:
   i. said at least one biologically active agent is a nucleic acid, and
   ii. said nanocapsule has a diameter of 60 nm to 150 nm.

10. The biodegradable multilayer nanocapsule according to claim 9, wherein dissolution of said core in step e) is achieved through incubation with a complexing agent.

11. The biodegradable multilayer nanocapsule according to claim 10, wherein said complexing agent is EDTA.

12. The biodegradable multilayer nanocapsule according to claim 9, wherein said nanocapsule preparation process further includes the steps of washing and centrifugation steps performed after one or more of steps a) to e).

13. The biodegradable multilayer nanocapsule according to claim 9, wherein said core-free nanocapsule comprises a void center.

14. The biodegradable multilayer nanocapsule according to claim 13, wherein said void center is free of active agent.

15. The biodegradable multilayer nanocapsule according to claim 9, characterized in that said first biodegradable polymer is dextran sulfate sodium salt and said second biodegradable polymer is poly-L-arginine-hydrochloride.

16. The biodegradable multilayer nanocapsule according to claim 9, characterized in that said nucleic acid is selected from among the group consisting of: an RNA, a synthetic analogue of RNA, a hybrid RNA/DNA molecule, an RNA molecule comprising non coding RNA, small non coding RNA, miRNA, long non coding RNA, siRNA, gRNA, and mRNA.

17. The biodegradable multilayer nanocapsule according to claim 13, characterized in that the nucleic acid is selected from among the group consisting of:
DNA, its synthetic analogues, and hybrid DNA/RNA molecules comprising linear fragments of DNA, circle DNA, plasmids, single- and double stranded DNA, RNA/DNA hybrids and synthetic nucleic acids which are able to bind intracellular DNA or RNA fragments.

* * * * *

SEQUENCE LISTING

```
<160> NUMBER OF SEQ ID NOS: 2

<210> SEQ ID NO 1
<211> LENGTH: 20
<212> TYPE: DNA
<213> ORGANISM: artificial sequence
<220> FEATURE:
<223> OTHER INFORMATION: primer

<400> SEQUENCE: 1
aggcagagag gggttaaggt                                              20

<210> SEQ ID NO 2
<211> LENGTH: 20
<212> TYPE: DNA
<213> ORGANISM: artificial sequence
```

```
<220> FEATURE:
<223> OTHER INFORMATION: primer

<400> SEQUENCE: 2
gggtcagacg tccaaaacca                                                20
```